US009540356B2

(12) United States Patent
Gillet et al.

(10) Patent No.: US 9,540,356 B2
(45) Date of Patent: Jan. 10, 2017

(54) COMPOUNDS HAVING A PROTECTIVE ACTIVITY AGAINST TOXINS WITH INTRACELLULAR ACTIVITY

(71) Applicants: COMMISSARIAT A L'ENERGIE ATOMIQUE ET AUX ENERGIES ALTERNATIVES, Paris (FR); INSTITUT CURIE, Paris (FR); CENTRE NATIONAL DE LA RECHERCHE SCIENTIFIQUE, Paris (FR)

(72) Inventors: Daniel Gillet, Paris (FR); Julien Barbier, Gif-sur-Yvette (FR); Ludger Johannes, Courbevoie (FR); Jean-Christophe Cintrat, Igny (FR); Romain Noel, Trevou-Treguinec (FR)

(73) Assignees: COMMISSARIAT A L'ENERGIE ATOMIQUE ET AUX ENERGIES ALTERNATIVES, Paris (FR); INSTITUT CURIE, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/436,737

(22) PCT Filed: Oct. 18, 2013

(86) PCT No.: PCT/EP2013/071863
§ 371 (c)(1),
(2) Date: Apr. 17, 2015

(87) PCT Pub. No.: WO2014/060586
PCT Pub. Date: Apr. 24, 2014

(65) Prior Publication Data
US 2015/0291568 A1    Oct. 15, 2015

(30) Foreign Application Priority Data

Oct. 19, 2012 (EP) .................................... 12306297

(51) Int. Cl.
| C07D 409/04 | (2006.01) |
| C07D 409/14 | (2006.01) |
| C07D 239/91 | (2006.01) |
| C07D 417/14 | (2006.01) |

(52) U.S. Cl.
CPC ........... *C07D 409/04* (2013.01); *C07D 239/91* (2013.01); *C07D 409/14* (2013.01); *C07D 417/14* (2013.01)

(58) Field of Classification Search
CPC .................................................... C07D 239/91
See application file for complete search history.

(56) References Cited

PUBLICATIONS

Jewn et al., Scientific Reports (Sep. 5, 2012), pp. 1-4.*
International Search Report issued Dec. 4, 2013, in PCT/EP2013/071863, filed Oct. 18, 2013.
Jewn Giew Park, et al., "Chemical Structure of Retro-2, a Compound That Protects Cells against Ribosome-Inactivating Proteins", Scientific Reports, vol. 2, XP 055053611, Sep. 5, 2012, 4 pages.
Khodabakhsh Niknam, et al., "Silica-bonded N-propylsulfamic acid as a recyclable catalyst for the synthesis of 2,3-dihydroquinazolin-4(1H)-ones", Chinese Chemical Letters, vol. 22, No. 1, XP 027559177, Jan. 2011, pp. 69-72.
Renato Noto, et al., "NMR Analysis of Restricted Internal Rotation in 2-Substituted-2,3-Dihydro-3-o-tolyl(chlorophenyl)-4(1H)-quinazolinones", Journal of Heterocyclic Chemistry, vol. 33, No. 4, XP 055063338, Jul.-Aug. 1996, pp. 1067-1071.
Lei Di-Wu, et al., "Identification of CK2 inhibitors with new scaffolds by a hybrid virtual screening approach based on Bayesian model; pharmacophore hypothesis and molecular docking", Journal of Molecular Graphics and Modelling, vol. 36, XP 028423237, Mar. 17, 2012, pp. 42-47.
Camille Locht, et al., "The ins and outs of pertussis toxin", FEBS Journal 278 (2011) 4668-4682 2011 The Authors Journal compilation 2011 FEBS, 15 pp.
Paton, A.W., et al., AB5 subtilase inactivates the endoplasmic reticulum chaperone BiP, Nature, Oct. 5, 2006; 443(7111):548-52, Abstract only.
Matthew J Walsh, et al., "Ribosome-inactivating Proteins Potent Poisons and Molecular Tools", Virulence 4:8, 774-784; Nov. 15, 2013; Landes Bioscience, 11 pp.
Lancer WI, "Retrocrade Transport of Cholera Toxin into the ER of Host Cells", Int J Med Microbial, Apr. 2004; 293(7-8); 491-4, Abstract only.
T. Secher, et al., "Retrograde Trafficking Inhibitor of Shiga Toxins Reduces Morbidity and Mortality of Mice Infected with Enterohemorrhagic *Escherichia coli*", Antimicrobial Agents and Chemotherapy, Aug. 2015 vol. 59 No. 8, 4 pp.
Bahne Stechmann, et al., "Inhibition of Retrograde Transport Protects Mice from Lethal Ricin Challenge", Cell 141, 231-242, Apr. 16, 2010 Elsevier Inc. 231, 12 pp.

\* cited by examiner

*Primary Examiner* — Paul V Ward
(74) *Attorney, Agent, or Firm* — Oblon, McClelland, Maier & Neustadt, L.L.P.

(57) ABSTRACT

The present invention concerns a new family of 2,3-dihydroquinazolin-4(1H)-one compounds of general formula (I), and the use thereof as inhibitors of the toxic effects of toxins with intracellular activity, such as ricin or Shiga toxin, for example, using retrograde transport to intoxicate cells.

12 Claims, 3 Drawing Sheets

Ricin

Chain A (RTA)
Chain B (RTB)

Subunit A (StxA)
Subunit B (StxB)

Stx-2

COMPOUNDS HAVING A PROTECTIVE ACTIVITY AGAINST TOXINS WITH INTRACELLULAR ACTIVITY

The subject of the present invention is a new family of 2,3-dihydroquinazolin-4(1H)-one compounds and the use thereof as inhibitors of the toxic effects of toxins with intracellular activity, for instance ricin, using retrograde transport to poison cells.

Toxins with intracellular activity which use retrograde transport represent a major public health problem and are associated with more than one million deaths each year throughout the world. These toxins are in particular ricin (produced in the seeds of the *Ricinus communis* plant), Shiga toxin and Shiga-like toxins (Stxs) produced by *Shigella dysenteriae* (Stx) and *E. coli* (Stx1 and Stx2), cholera toxin (Ctx *Vibrio cholerae* responsible for cholera), pertussis toxin (*Bordetella pertussis*, the agent responsible for whooping cough), subtilase cytotoxin and thermolabile enterotoxin (*E. coli*).

Ricin is a 66 kDa glycoprotein composed of two polypeptide chains linked by a disulfide bridge (FIG. 1A). The B chain (RTB, lectin of 262 residues) allows the toxin to bind to cell membrane glycolipids and glycoproteins and ensures its entry into the cell (FIG. 1A). The A chain (RTA, 267 amino acids) provides the N-glycosidase enzymatic function of ricin, catalyzes the removal of adenine 4324 of the 28S RNA of the targeted cells and causes the arrest of protein synthesis.

Shiga toxins include the Shiga toxin (Stx) produced by *Shigella dysenteriae* and the Shiga-like 1 (Stx1) and 2 (Stx2) toxins produced by the enterohemorrhagic strains of *E. coli*. The Stx and Stx1 toxins are 99% identical, while Stx1 and Stx2 share only 56% identity of their amino acid sequence. The A subunit of the toxin (StxA) carries the same enzymatic activity as ricin and identically targets the 28S RNA (FIG. 1B). The B subunit (StxB), which is in pentameric form, allows binding of the toxin with the cell via its interaction with globotriaosylceramide Gb3, which ensures its internalization and its intracellular trafficking.

After binding to its membrane receptors, ricin is internalized into these cells via multiple endocytosis pathways and reaches the trans-Golgi network where it is conveyed to the endoplasmic reticulum (ER) by retrograde transport (FIG. 2A). Shiga toxins are, for their part, internalized via a single endocytosis pathway and also reach the Golgi apparatus and then the endoplasmic reticulum (FIG. 2B).

The toxins are then partially unfolded and the A chain/subunit is translocated into the cytosol (Lord, J. M. et al., *Biochemical Society Transactions* 2003, 31, 1260). The ultimate step of the action of these toxins thus takes place in the cell cytoplasm; the toxins bind to ribosomes with great efficiency and cleave adenine 4324 of the 28S RNA of the 60S subunit of the ribosome. This depurination of the 28S RNA causes the arrest of protein synthesis and leads to cell death.

To counter the threat posed by these toxins, several types of antitoxins have been developed: neutralizing antibodies, enzymatic activity inhibitors (small molecules, substrate analogs), soluble receptor mimetics and chemical compounds which act on the cells targeted by the toxin:

- Small molecules which inhibit the enzymatic activity of ricin (Miller, D. et al., *J. Med. Chem* 2002, 45, 90 and Yan, X. et al., *J. Mol. Biol.* 1997, 266, 1043).
- Small molecules which inhibit the enzymatic activity of Stx (Brigotti M. et al., *Nucleic Acids Res.* 2000, 28 (12), 2383).

- RNA derivatives: since ricin recognizes a very precise sequence in the 28S RNA, the SRL loop (Sarcin-Ricin Loop), inhibitors have been designed on the basis of this nucleotide sequence (Schramm et al. *Biochemistry* 2001, 40 (23), 6845; Roday, S. et al., *Biochemistry* 2004, 43, 4923; Hesselberth, J. R. et al., *J. Biol. Chem.* 2000, 275, 4937, Fan, S. et al., *World J. Gastroenterol.* 2008, 14, 6360).
- Antibodies directed against ricin (Lemley, P. V. et al., *Hybridoma* 1994, 13, 417; Guo, J. W. et al., *Hybridoma* 2005, 24, 263; Pelat, T. et al., *BMC Biotechnol.* 2009, 9, 60).
- Antibodies directed against Stx (Sheoran A. S. et al., *Infect Immun.* 2005, 73, 4607-13; Tzipori S. et al., *Clin. Microbiol. Rev.* 2004 17, 926-41).
- Soluble mimetics of ricin receptors (Perera L. P. et al., *J Clin Microbiol.* 1988, 26, 2127-31; Smith M. J. et al., *Infect Immun.* 2006, 74, 6992-8).
- Soluble mimetics of Stx receptors (Armstrong G. D. et al., *J. Infect. Dis.* 1995, 171, 1042-5; Trachtman H. et al., *JAMA* 2003, 290, 1337-44; Kitov P. I. et al., *Nature* 2000, 403, 669-72; Nishikawa K. et al., *PNAS* 2002, 99, 7669-74; Mulvey G. L. et al., *J. Infect. Dis.* 2003, 187, 640-9; Watanabe et al., *J. Infect. Dis.* 2004, 189, 360-8).
- Vaccine approach for controlling the effects of ricin: a certain number of vaccines have been described in particular in scientific patents and publications. They claim protection against ricin via the administration of an immunogenic amount of RTA or RTB derivatives.
- Vaccine approach for controlling the effects of Stx: a vaccine that is effective in humans should result in the production of antibodies preventing the colonization of bacteria in the intestinal tract or neutralizing the Shiga toxins produced, in order to prevent the development of hemolytic uremic syndrome. Such a vaccine is not available at the current time, even though research studies are currently being carried out in this direction.

Over the past few years, research for new molecules aimed at blocking intracellular trafficking of toxins with intracellular activity has accelerated. The main advantage of molecules of this type is their broad-spectrum activity since these molecules can efficiently protect cells against the various toxins which use the retrograde pathway.

However, these molecules, such as Brefeldin A (Donta S. T. et al., *J. Infect. Dis.* 1995 171, 721-4), Exo2 (Spooner R. A. et al., *Biochem J.* 2008, 414, 471-84; Yarrow J. C. et al., *C.C.H.T.S.* 2003, 6, 279-86), Golgicide (Saenz J. B. et al., *Nat. Chem. Biol.* 2009, 5, 157-65) and others (Saenz J. B. et al., *Infect. Imm.* 2007, 75, 4552-61), even though they protect cells against the action of toxins with intracellular activity, are themselves cytotoxic since they target key functions of cell homeostasis and cannot therefore be used for therapeutic purposes.

Other molecules have been identified, in particular by high-throughput screening, as the inhibitor of the action of ricin and/or of Stxs: compounds 134 and 75 (Saenz J. B. et al., *Infect. Imm.* 2007, 75, 4552-61) (see the scheme hereinafter). The cellular target of these molecules remains unknown; they appear to block ricin and Stx transport inside the cells. However, these compounds do not protect A549 human pulmonary epithelial cells and none of these molecules has shown a protective effect in animals. Furthermore, these molecules modify the morphology of the Golgi apparatus, thereby indicating, on the one hand, a different mechanism of action and, on the other hand, an intrinsic toxicity of the compounds.

High-throughput screening has also made it possible to identify the compounds Retro-1 and Retro-2 (EP2145873, WO2009/153457, WO2009/153665, Stechmann B. et al., *Cell* 2010, 141, 231-42) as ricin and/or Stx inhibitors; these compounds are capable of protecting A549 human pulmonary epithelial cells; in addition Retro-2 has shown efficacy in animals.

Another research team has identified new molecules which protect against ricin and Stxs, also during high-throughput screening on Vero cells (Wahome P. G. et al., *Toxicon* 2010, 56, 313-23). These compounds (CID 644401, CID 5737931 and CID 18576762) do not appear to be as active (EC50 between 25 and 60 μM) as the Retro-1 and Retro-2 compounds and their mode of action remains unknown.

A. Inhibitors with an Identified Cell Target

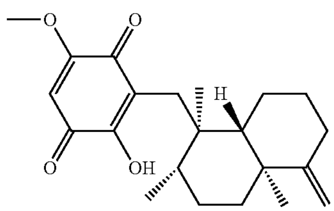

Ilimaquinone

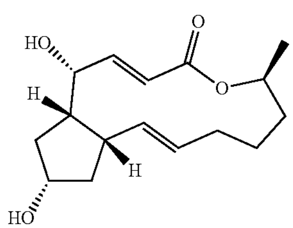

Brefeldin A

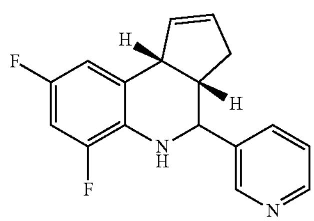

Gogicide A

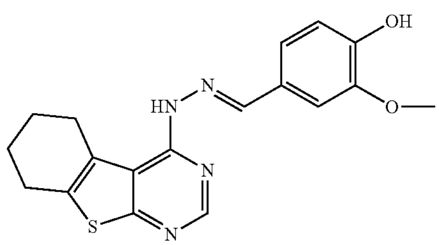

Exo2

-continued

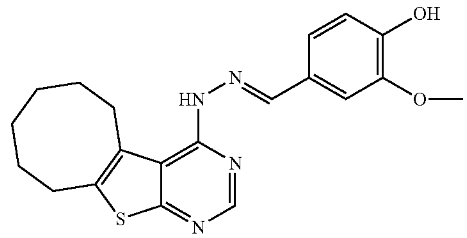

LG186

B. Inhibitors of which the Cell Target is Unknown

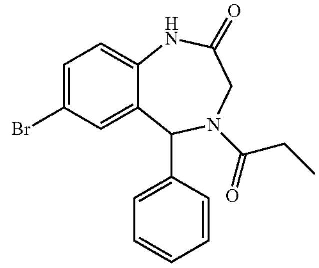

Retro-1

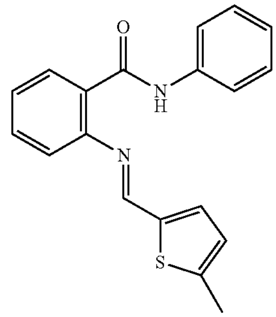

Retro-2

Compound 134

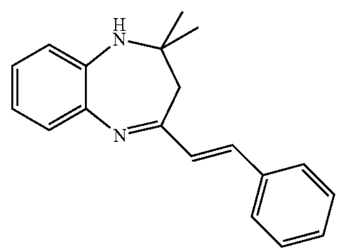

Compound 75

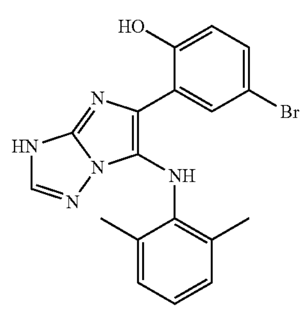

-continued

Compound 2

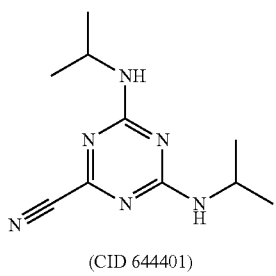
(CID 644401)
Compound 3
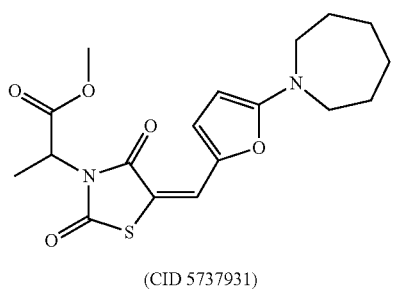
(CID 5737931)
Compound 4
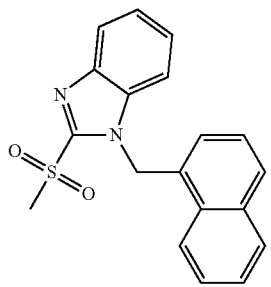
(CID 18576762)

Small Molecules with Intracellular Activity which Inhibit the Action of Ricin and/or of Stxs Very recently, the team of Park et al. [Park et al. Chemical Structure of Retro-2, a Compound That Protects Cells against Ribosome-Inactivating Proteins. *Nature Scientific Reports*. 2012. 2; 631] has studied the chemical structure of Retro-2 and has demonstrated the spontaneous cyclization of this compound and shown that it is in this cyclized form that Retro-2 exercises a protective activity on cells against the toxins.

In the context of its research on compounds which block retrograde transport and more particularly of studies on compounds derived from cyclized Retro-2, carried out in parallel with the abovementioned studies, the applicant has identified a new family of compounds derived from 2,3-dihydroquinazolin-4(1H)-one which exhibit a biological activity greater than that of cyclized Retro-2 and therefore a marked value for the prevention and/or treatment of poisoning with at least one toxin with an intracellular mode of action using retrograde transport to infect mammalian eukaryotic cells.

Thus, the present invention relates to compounds of general formula (I):

(I)

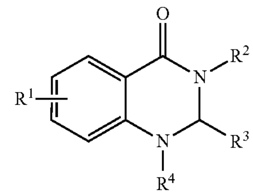

wherein $R^1$ represents a hydrogen atom, a halogen atom or an alkoxy radical having from 1 to 3 carbon atoms;

$R^2$ represents:

- a phenyl radical, optionally substituted with: a phenyl radical, a $—CF_3$ group, a halogen atom, an $—SO_2$-phenyl group or an —S—X or —O—X group, X being an alkyl radical having from 1 to 4 carbon atoms, preferably a methyl radical, an alkoxy having from 1 to 4 carbon atoms or a PEG of formula $—(CH_2—CH_2—O)_n—R$ with n being 1 to 10, preferably n is 1, and R represents a hydrogen atom or a methyl radical, preferably R is a methyl radical, or a —CO—Y or —CO—O—Y group, Y being chosen from a hydrogen atom, an alkyl radical having from 1 to 4 carbon atoms, a phenyl ring or an allyl ($—CH_2—CH{=}CH_2$) group;
  - a heterocycle or a heterobicycle having from 5 to 10 atoms comprising one or two nitrogen atoms, preferably a pyridine radical;
  - an adamantyl ring, optionally substituted with a hydroxyl function;

$R^3$ represents:

- an aromatic heterocycle having 5 or 6 atoms, which may be chosen from a thiophene, furan, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine or pyrazine ring, preferably a thiophene or pyridine ring;
- said heterocycle being substituted with:
  - an alkyl radical having from 1 to 3 carbon atoms, preferably a methyl radical;
  - a halogen atom;
  - a phenyl radical optionally substituted with an alkoxy radical having from 1 to 3 carbon atoms, a —CN group, an $—NO_2$ group or a —COX or —COOX group with X an alkyl radical having from 1 to 4 carbon atoms, or a combination of these substituents, preferably a methyl radical;
  - a —SY group, Y being an alkyl radical having from 1 to 4 carbon atoms or a phenyl radical;
  - a —CN group;
  - a $—CH_2—N_3$ group;
  - an aromatic heterocycle having 5 or 6 atoms, which may be chosen from a furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine or pyrazine ring, preferably said heterocycle having 5 or 6 atoms is a thiophene, a pyridine, a furan or a thiazole; optionally substituted with at least one alkyl radical having from 1 to 3 carbon atoms and/or a $—CH_2—N_3$ group;

a phenyl radical; optionally substituted with an alkoxy radical having from 1 to 3 carbon atoms or an NMe$_2$ group;

R$^4$ represents a hydrogen atom or a methyl radical;

with the exception of the compound such that R$^1$ is a hydrogen atom, R$^2$ a phenyl radical, R$^3$ a 5-methylthiophen-2-yl radical and R$^4$ a hydrogen atom, and the pharmaceutically acceptable salts thereof.

The present invention relates to the compounds of general formula (I) as such and also to the use thereof for the prevention and/or treatment of disorders induced by toxins with intracellular activity using retrograde transport.

The present invention also relates to a method for preventing and/or treating disorders induced by toxins with intracellular activity using retrograde transport and comprising the administration of an effective amount of at least one compound of general formula (I).

Preferably, the following compounds of general formula (I): 3-(4-chlorophenyl)-2-(5-methylthiophen-2-yl)-2,3-dihydroquinazolin-4(1H)-one;

R$^1$=—H; R$^2$=pyridinyl; R$^3$=3,4-dimethoxyphenyl and R$^4$=—H;
R$^1$=—H; R$^2$=methoxyphenyl; R$^3$=pyridinyl and R$^4$=—H;
R$^1$=—H; R$^2$=phenyl; R$^3$=6-methyl-2-pyridinyl and R$^4$=—H;
R$^1$=—H; R$^2$=methoxyphenyl; R$^3$=dimethylaminophenyl and R$^4$=—H;
R$^1$=—H; R$^2$=phenyl; R$^3$=furanyl and R$^4$=—H;
R$^1$=—H; R$^2$=phenyl-phenyl; R$^3$=methoxyphenyl and R$^4$=—H;
R$^1$=—H; R$^2$=phenyl; R$^3$=dimethylaminophenyl and R$^4$=—H;
R$^1$=—H; R$^2$=phenyl; R$^3$=phenyl and R$^4$=—H;
R$^1$=—H; R$^2$=4-chlorophenyl; R$^3$=5-methyl-2-thienyl and R$^4$=—H;
R$^1$=—H; R$^2$=phenyl; R$^3$=methoxyphenyl and R$^4$=—H;

and those such that R$^2$ is a substituted phenyl and R$^3$ a furan ring, a substituted phenyl or a pyridine;

as such are excluded from the subject of the present invention; on the other hand, the use thereof for therapeutic purposes, in particular for the prevention and/or treatment of disorders induced by toxins with intracellular activity using retrograde transport is indeed a subject of the present invention.

The term "pharmaceutically acceptable salt of the compounds of general formula (I)" is intended to mean the hydrochlorides, hydrobromides, sulfates or bisulfates, phosphates or hydrogen phosphates, acetates, oxalates, benzoates, succinates, fumarates, maleates, lactates, citrates, tartrates, gluconates, methanesulfonates, benzenesulfonates and para-toluenesulfonates.

The term "halogen atom" is intended to mean the chemical elements of group VII of the Periodic Table of the elements, in particular fluorine, chlorine, bromine and iodine.

The term "alkyl radical having from 1 to 3 or 4 carbon atoms" denotes a linear or branched hydrocarbon-based radical; mention may, for example, be made of methyl, ethyl, propyl, isopropyl or tert-butyl.

The term "alkoxy radical having from 1 to 3 or 4 carbon atoms" is intended to mean an —OC$_n$H$_{2n+1}$ radical, n being an integer between 1 and 3 or 4; mention may, for example, be made of the methoxy, ethoxy, propyloxy or isopropyloxy radical. Preferably, n is 1.

More particularly, the compounds of general formula (I) are chosen from table I hereinafter:

| Molecule | Compound | Structure | Name |
| --- | --- | --- | --- |
| RN-1-013 | 1 | 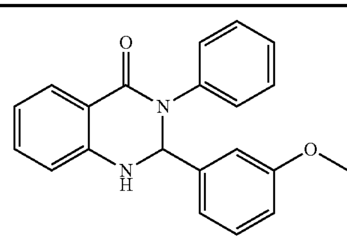 | 2-(3-Methoxyphenyl)-3-phenyl-2,3-dihydroquinazolin-4(1H)-one |
| RN-1-019 | 2 | 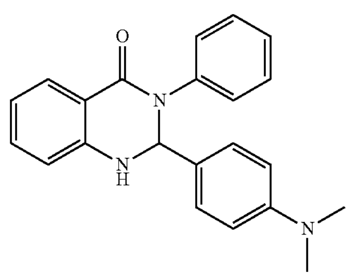 [SMILES: CN(C)c1ccc(C2Nc3ccccc3C(=O)N2c2ccccc2)cc1] | 2-(4-(Dimethylamino)phenyl)-3-phenyl-2,3-dihydroquinazolin-4(1H)-one |
| RN-1-021 | 3 | 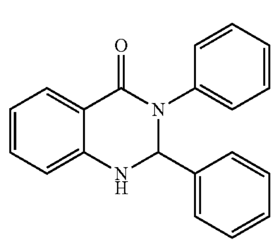 [SMILES: O=C1c2ccccc2NC(c2ccccc2)N1c1ccccc1] | 2,3-Diphenyl-2,3-dihydroquinazolin-4(1H)-one |

-continued

| Molecule | Compound | Structure | Name |
|---|---|---|---|
| RN-1-027 | 4 | 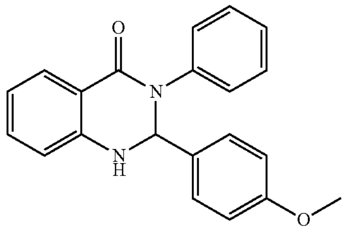 [SMILES: COc1ccc(C2Nc3ccccc3C(=O)N2c2ccccc2)cc1] | 2-(4-Methoxyphenyl)-3-phenyl-2,3-dihydroquinazolin-4(1H)-one |
| RN-1-066 | 5 | 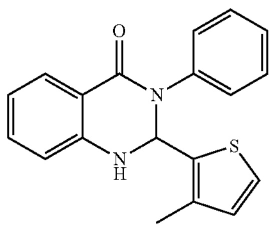 [SMILES: Cc1ccsc1C1Nc2ccccc2C(=O)N1c1ccccc1] | 2-(3-Methylthiophen-2-yl)-3-phenyl-2,3-dihydroquinazolin-4(1H)-one |
| RN-1-067 | 6 | 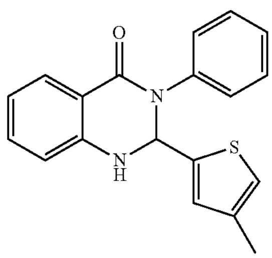 [SMILES: Cc1csc(C2Nc3ccccc3C(=O)N2c2ccccc2)c1] | 2-(4-Methylthiophen-2-yl)-3-phenyl-2,3-dihydroquinazolin-4(1H)-one |
| RN-1-068 | 7 | 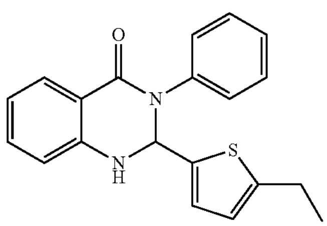 [SMILES: CCc1ccc(C2Nc3ccccc3C(=O)N2c2ccccc2)s1] | 2-(5-Ethylthiophen-2-yl)-3-phenyl-2,3-dihydroquinazolin-4(1H)-one |
| RN-1-086 | 8 | 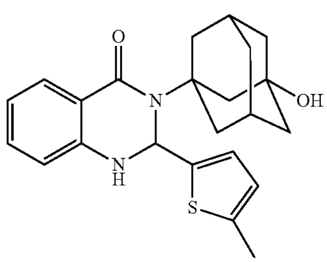 [SMILES: Cc1ccc(C2Nc3ccccc3C(=O)N2C23CC4CC(CC(O)(C4)C2)C3)s1] | 3-((5R,7S)-3-Hydroxyadamantan-1-yl)-2-(5-methylthiophen-2-yl)-2,3-dihydroquinazolin-4(1H)-one |
| RN-1-100 | 9 | 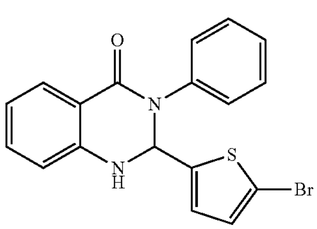 [SMILES: O=C1c2ccccc2NC(c2ccc(Br)s2)N1c1ccccc1] | 2-(5-Bromothiophen-2-yl)-3-phenyl-2,3-dihydroquinazolin-4(1H)-one |

-continued

| Molecule | Compound | Structure | Name |
| --- | --- | --- | --- |
| RN-1-118 | 10 | 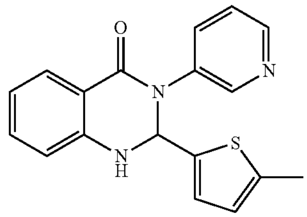 [SMILES: Cc1ccc(C2Nc3ccccc3C(=O)N2c2cccnc2)s1] | 2-(5-Methylthiophen-2-yl)-3-(pyridin-3-yl)-2,3-dihydroquinazolin-4(1H)-one |
| RN-1-120 | 11 | 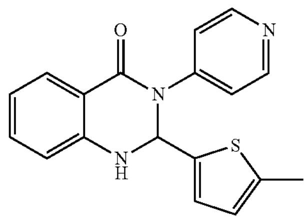 [SMILES: Cc1ccc(C2Nc3ccccc3C(=O)N2c2ccncc2)s1] | 2-(5-Methylthiophen-2-yl)-3-(pyridin-4-yl)-2,3-dihydroquinazolin-4(1H)-one |
| RN-1-132 | 12 | 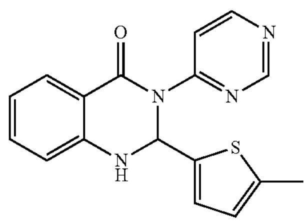 [SMILES: Cc1ccc(C2Nc3ccccc3C(=O)N2c2ccncn2)s1] | 2-(5-Methylthiophen-2-yl)-3-(pyrimidin-4-yl)-2,3-dihydroquinazolin-4(1H)-one |
| RN-1-148 | 13 | 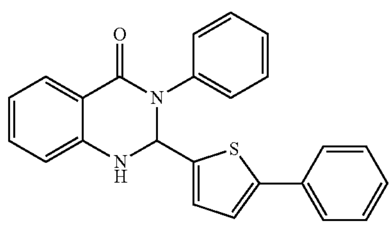 [SMILES: O=C1c2ccccc2NC(c2ccc(-c3ccccc3)s2)N1c1ccccc1] | 3-Phenyl-2-(5-phenylthiophen-2-yl)-2,3-dihydroquinazolin-4(1H)-one |
| RN-1-149 | 14 | 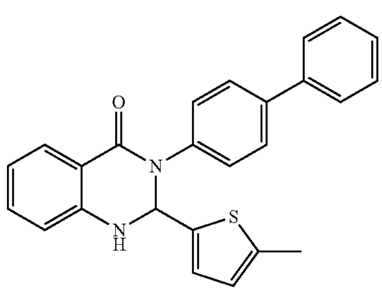 [SMILES: Cc1ccc(C2Nc3ccccc3C(=O)N2c2ccc(-c3ccccc3)cc2)s1] | 3-([1,1'-Biphenyl]-4-yl)-2-(5-methylthiophen-2-yl)-2,3-dihydroquinazolin-4(1H)-one |
| RN-1-151 | 15 | 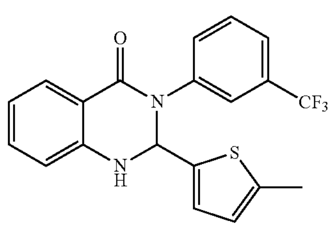 [SMILES: Cc1ccc(C2Nc3ccccc3C(=O)N2c2cccc(C(F)(F)F)c2)s1] | 2-(5-Methylthiophen-2-yl)-3-(3-(trifluoromethyl)phenyl)-2,3-dihydroquinazolin-4(1H)-one |

-continued

| Molecule | Compound | Structure | Name |
|---|---|---|---|
| RN-1-162 | 16 | 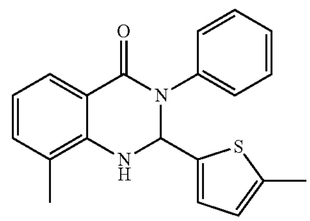 [SMILES: Cc1ccc(C2Nc3c(C)cccc3C(=O)N2c2ccccc2)s1] | 8-Methyl-2-(5-methylthiophen-2-yl)-3-phenyl-2,3-dihydroquinazolin-4(1H)-one |
| RN-1-173 | 17 | 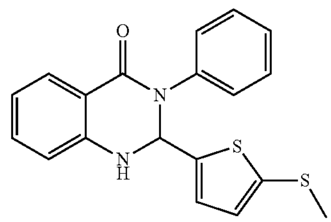 [SMILES: CSc1ccc(C2Nc3ccccc3C(=O)N2c2ccccc2)s1] | 2-(5-(Methylthio)thiophen-2-yl)-3-phenyl-2,3-dihydroquinazolin-4(1H)-one |
| RN-1-174 | 18 | 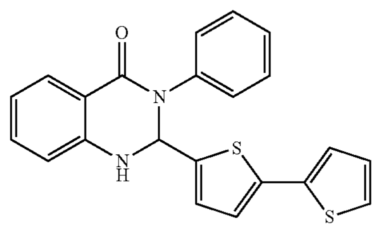 [SMILES: O=C1c2ccccc2NC(c2ccc(-c3cccs3)s2)N1c1ccccc1] | 2-([2,2'-Bithiophen]-5-yl)-3-phenyl-2,3-dihydroquinazolin-4(1H)-one |
| RN-1-175 | 19 | 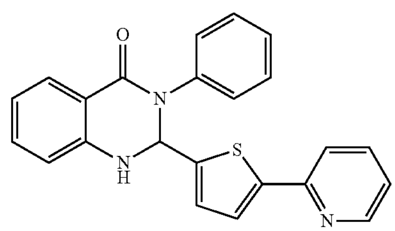 [SMILES: O=C1c2ccccc2NC(c2ccc(-c3ccccn3)s2)N1c1ccccc1] | 3-Phenyl-2-(5-(pyridin-2-yl)thiophen-2-yl)-2,3-dihydroquinazolin-4(1H)-one |
| RN-1-176 | 20 | 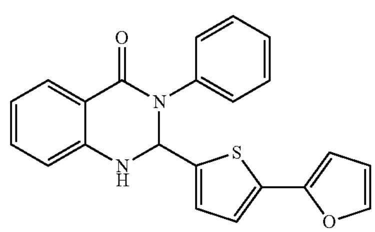 [SMILES: O=C1c2ccccc2NC(c2ccc(-c3ccco3)s2)N1c1ccccc1] | 2-(5-(Furan-2-yl)thiophen-2-yl)-3-phenyl-2,3-dihydroquinazolin-4(1H)-one |
| RN-1-177 | 21 | 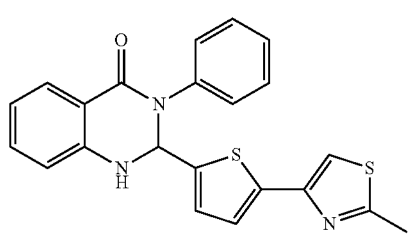 [SMILES: Cc1nc(-c2ccc(C3Nc4ccccc4C(=O)N3c3ccccc3)s2)cs1] | 2-(5-(2-Methylthiazol-4-yl)thiophen-2-yl)-3-phenyl-2,3-dihydroquinazolin-4(1H)-one |
| RN-2-120 | 22 | 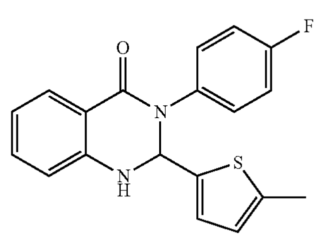 [SMILES: Cc1ccc(C2Nc3ccccc3C(=O)N2c2ccc(F)cc2)s1] | 3-(4-Fluorophenyl)-2-(5-methylthiophen-2-yl)-2,3-dihydroquinazolin-4(1H)-one |

-continued

| Molecule | Compound | Structure | Name |
|---|---|---|---|
| RN-2-137 | 23 | 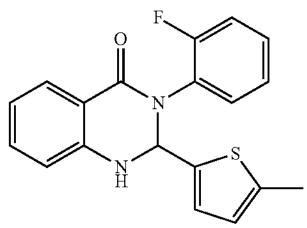 [SMILES: Cc1ccc(C2Nc3ccccc3C(=O)N2c2ccccc2F)s1] | 3-(2-Fluorophenyl)-2-(5-methylthiophen-2-yl)-2,3-dihydroquinazolin-4(1H)-one |
| RN-2-161 | 24 | 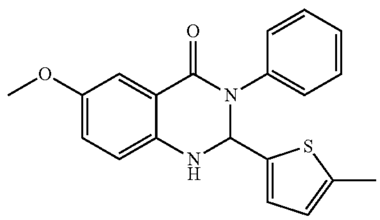 | 6-Methoxy-2-(5-methylthiophen-2-yl)-3-phenyl-2,3-dihydroquinazolin-4(1H)-one |
| RN-2-162 | 25 | 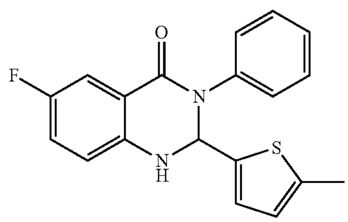 [SMILES: Cc1ccc(C2Nc3ccc(F)cc3C(=O)N2c2ccccc2)s1] | 6-Fluoro-2-(5-methylthiophen-2-yl)-3-phenyl-2,3-dihydroquinazolin-4(1H)-one |
| RN-2-163 | 26 | 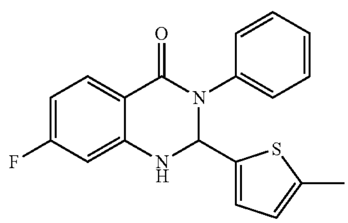 [SMILES: Cc1ccc(C2Nc3cc(F)ccc3C(=O)N2c2ccccc2)s1] | 7-Fluoro-2-(5-methylthiophen-2-yl)-3-phenyl-2,3-dihydroquinazolin-4(1H)-one |
| RN-2-177 | 27 | 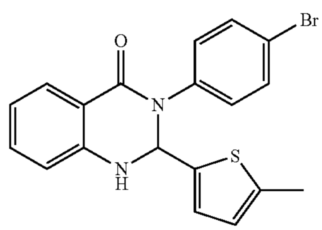 [SMILES: Cc1ccc(C2Nc3ccccc3C(=O)N2c2ccc(Br)cc2)s1] | 3-(4-Bromophenyl)-2-(5-methylthiophen-2-yl)-2,3-dihydroquinazolin-4(1H)-one |
| RN-2-178 | 28 | 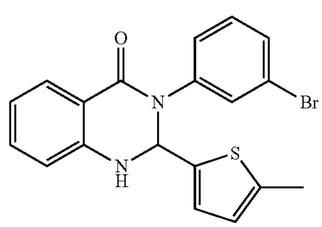 [SMILES: Cc1ccc(C2Nc3ccccc3C(=O)N2c2cccc(Br)c2)s1] | 3-(3-Bromophenyl)-2-(5-methylthiophen-2-yl)-2,3-dihydroquinazolin-4(1H)-one |
| RN-2-180 | 29 | 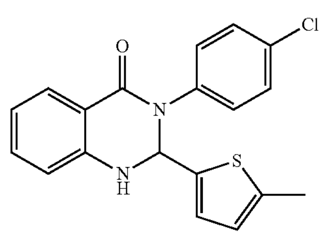 [SMILES: Cc1ccc(C2Nc3ccccc3C(=O)N2c2ccc(Cl)cc2)s1] | 3-(4-Chlorophenyl)-2-(5-methylthiophen-2-yl)-2,3-dihydroquinazolin-4(1H)-one |

-continued

| Molecule | Compound | Structure | Name |
| --- | --- | --- | --- |
| RN-2-181 | 30 | 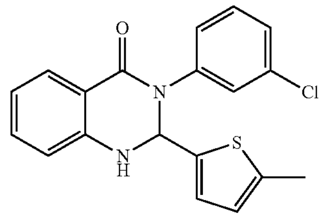 [SMILES: Cc1ccc(C2Nc3ccccc3C(=O)N2c2cccc(Cl)c2)s1] | 3-(3-Chlorophenyl)-2-(5-methylthiophen-2-yl)-2,3-dihydroquinazolin-4(1H)-one |
| RN-2-183 | 31 | 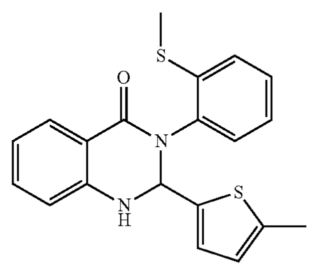 [SMILES: CSc1ccccc1N1C(=O)c2ccccc2NC1c1ccc(C)s1] | 3-(2-(Methylthio)phenyl)-2-(5-methylthiophen-2-yl)-2,3-dihydroquinazolin-4(1H)-one |
| RN-2-182 | 32 | 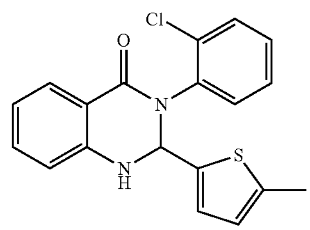 | 3-(2-Chlorophenyl)-2-(5-methylthiophen-2-yl)-2,3-dihydroquinazolin-4(1H)-one |
| RN-2-199 | 33 | 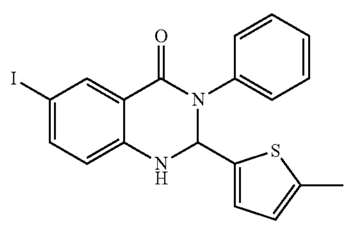 [SMILES: Cc1ccc(C2Nc3ccc(I)cc3C(=O)N2c2ccccc2)s1] | 6-Iodo-2-(5-methylthiophen-2-yl)-3-phenyl-2,3-dihydroquinazolin-4(1H)-one |
| RN-3-121 | 34 | 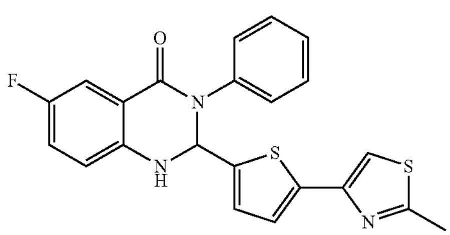 [SMILES: Cc1nc(-c2ccc(C3Nc4ccc(F)cc4C(=O)N3c3ccccc3)s2)cs1] | 6-Fluoro-2-(5-(2-methylthiazol-4-yl)thiophen-2-yl)-3-phenyl-2,3-dihydroquinazolin-4(1H)-one |
| RN-1-181 | 35 | 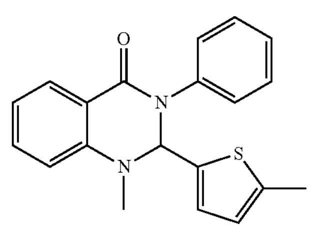 [SMILES: Cc1ccc(C2N(C)c3ccccc3C(=O)N2c2ccccc2)s1] | 1-Methyl-2-(5-methylthiophen-2-yl)-3-phenyl-2,3-dihydroquinazolin-4(1H)-one |

-continued

| Molecule | Compound | Structure | Name |
| --- | --- | --- | --- |
| RN-1-186 | 36 | 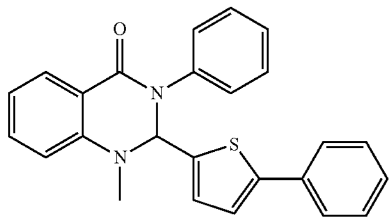 [SMILES: CN1c2ccccc2C(=O)N(c2ccccc2)C1c1ccc(-c2ccccc2)s1] | 1-Methyl-3-phenyl-2-(5-phenylthiophen-2-yl)-2,3-dihydroquinazolin-4(1H)-one |
| RN-1-192 | 37 | 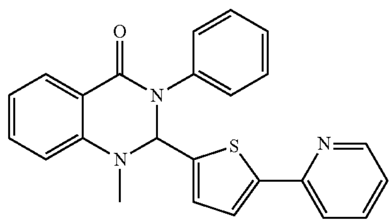 | 1-Methyl-3-phenyl-2-(5-(pyridin-2-yl)thiophen-2-yl)-2,3-dihydroquinazolin-4(1H)-one |
| RN-1-196 | 38 | 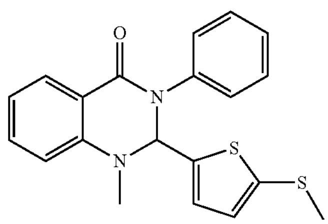 [SMILES: CSc1ccc(C2N(C)c3ccccc3C(=O)N2c2ccccc2)s1] | 1-Methyl-2-(5-(methylthio)thiophen-2-yl)-3-phenyl-2,3-dihydroquinazolin-4(1H)-one |
| RN-1-197 | 39 | 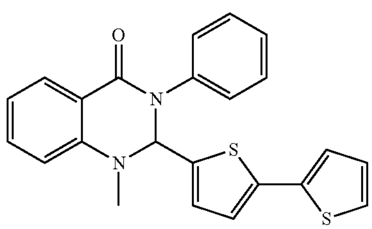 [SMILES: CN1c2ccccc2C(=O)N(c2ccccc2)C1c1ccc(-c2cccs2)s1] | 2-([2,2'-Bithiophen]-5-yl)-1-methyl-3-phenyl-2,3-dihydroquinazolin-4(1H)-one |
| RN-2-001 | 40 | 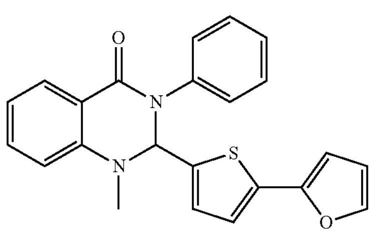 [SMILES: CN1c2ccccc2C(=O)N(c2ccccc2)C1c1ccc(-c2ccco2)s1] | 2-(5-(Furan-2-yl)thiophen-2-yl)-1-methyl-3-phenyl-2,3-dihydroquinazolin-4(1H)-one |
| RN-2-005 | 41 | 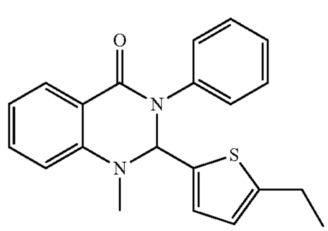 [SMILES: CCc1ccc(C2N(C)c3ccccc3C(=O)N2c2ccccc2)s1] | 2-(5-Ethylthiophen-2-yl)-1-methyl-3-phenyl-2,3-dihydroquinazolin-4(1H)-one |

| Molecule | Compound | Structure | Name |
| --- | --- | --- | --- |
| RN-2-015 | 42 | 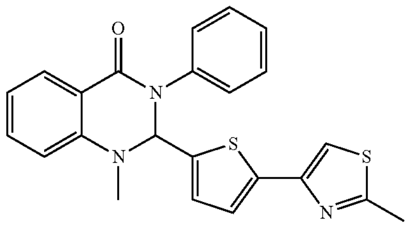 [SMILES: Cc1nc(-c2ccc(C3N(C)c4ccccc4C(=O)N3c3ccccc3)s2)cs1] | 1-Methyl-2-(5-(2-methylthiazol-4-yl)thiophen-2-yl)-3-phenyl-2,3-dihydroquinazolin-4(1H)-one |
| RN-2-016 | 43 | 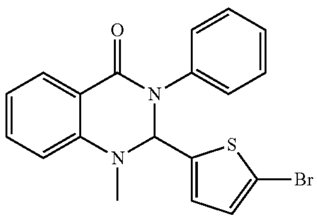 [SMILES: CN1c2ccccc2C(=O)N(c2ccccc2)C1c1ccc(Br)s1] | 2-(5-Bromothiophen-2-yl)-1-methyl-3-phenyl-2,3-dihydroquinazolin-4(1H)-one |
| RN-2-019 | 44 | 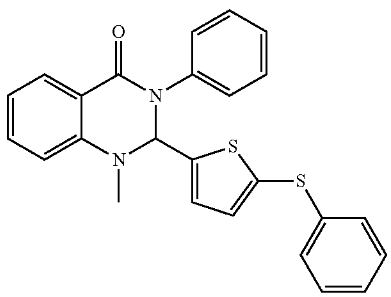 [SMILES: CN1c2ccccc2C(=O)N(c2ccccc2)C1c1ccc(Sc2ccccc2)s1] | 1-Methyl-3-phenyl-2-(5-(phenylthio)thiophen-2-yl)-2,3-dihydroquinazolin-4(1H)-one |
| RN-2-029 | 45 | 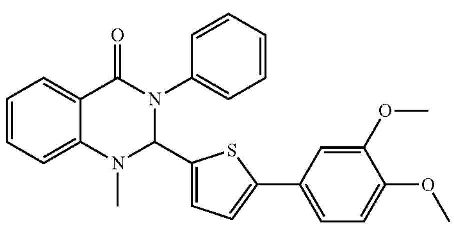 [SMILES: COc1ccc(-c2ccc(C3N(C)c4ccccc4C(=O)N3c3ccccc3)s2)cc1OC] | 2-(5-(3,4-Dimethoxyphenyl)thiophen-2-yl)-1-methyl-3-phenyl-2,3-dihydroquinazolin-4(1H)-one |
| RN-2-032 | 46 | 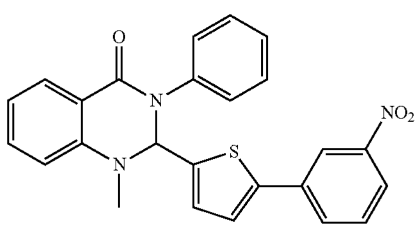 [SMILES: CN1c2ccccc2C(=O)N(c2ccccc2)C1c1ccc(-c2cccc([N+](=O)[O-])c2)s1] | 1-Methyl-2-(5-(3-nitrophenyl)thiophen-2-yl)-3-phenyl-2,3-dihydroquinazolin-4(1H)-one |
| RN-2-034 | 47 | 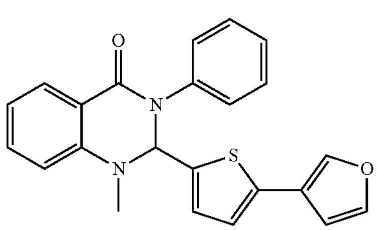 [SMILES: CN1c2ccccc2C(=O)N(c2ccccc2)C1c1ccc(-c2ccoc2)s1] | 2-(5-(Furan-3-yl)thiophen-2-yl)-1-methyl-3-phenyl-2,3-dihydroquinazolin-4(1H)-one |

-continued

| Molecule | Compound | Structure | Name |
|---|---|---|---|
| RN-2-049 | 48 | 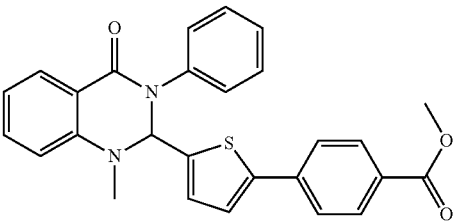 [SMILES: COC(=O)c1ccc(-c2ccc(C3N(C)c4ccccc4C(=O)N3c3ccccc3)s2)cc1] | Methyl 4-(5-(1-methyl-4-oxo-3-phenyl-1,2,3,4-tetrahydroquinazolin-2-yl)thiophen-2-yl)benzoate |
| RN-2-050 | 49 | 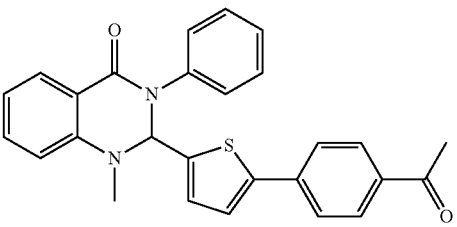 [SMILES: CC(=O)c1ccc(-c2ccc(C3N(C)c4ccccc4C(=O)N3c3ccccc3)s2)cc1] | 2-(5-(4-Acetylphenyl)thiophen-2-yl)-1-methyl-3-phenyl-2,3-dihydroquinazolin-4(1H)-one |
| RN-2-053 | 50 | 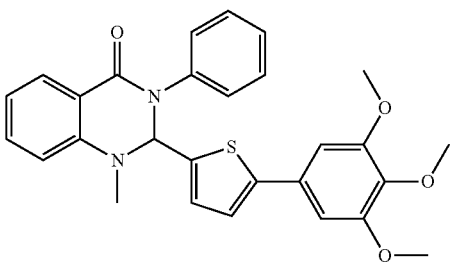 [SMILES: COc1cc(-c2ccc(C3N(C)c4ccccc4C(=O)N3c3ccccc3)s2)cc(OC)c1OC] | 1-Methyl-3-phenyl-2-(5-(3,4,5-trimethoxyphenyl)thiophen-2-yl)-2,3-dihydroquinazolin-4(1H)-one |
| RN-2-057 | 51 | 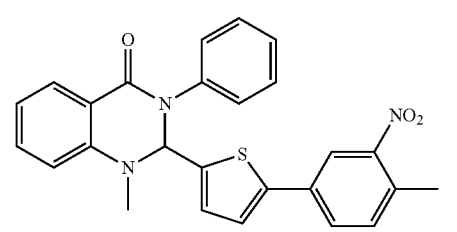 [SMILES: Cc1ccc(-c2ccc(C3N(C)c4ccccc4C(=O)N3c3ccccc3)s2)cc1[N+](=O)[O-]] | 1-Methyl-2-(5-(4-methyl-3-nitrophenyl)thiophen-2-yl)-3-phenyl-2,3-dihydroquinazolin-4(1H)-one |
| RN-2-059 | 52 | 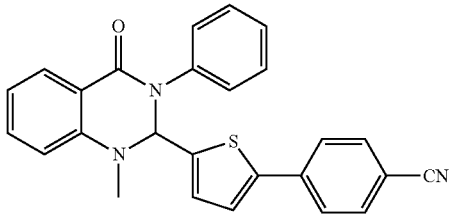 [SMILES: CN1c2ccccc2C(=O)N(c2ccccc2)C1c1ccc(-c2ccc(C#N)cc2)s1] | 4-(5-(1-Methyl-4-oxo-3-phenyl-1,2,3,4-tetrahydroquinazolin-2-yl)thiophen-2-yl)benzonitrile |
| RN-3-012 | 53 | 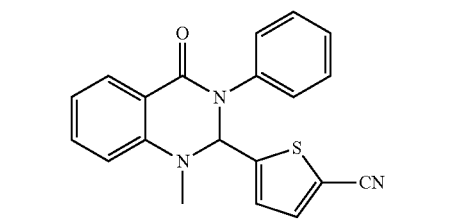 [SMILES: CN1c2ccccc2C(=O)N(c2ccccc2)C1c1ccc(C#N)s1] | 5-(1-Methyl-4-oxo-3-phenyl-1,2,3,4-tetrahydroquinazolin-2-yl)thiophene-2-carbonitrile |

| Molecule | Compound | Structure | Name |
| --- | --- | --- | --- |
| RN-3-066 | 54 | 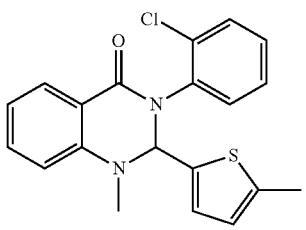 [SMILES: Cc1ccc(C2N(C)c3ccccc3C(=O)N2c2ccccc2Cl)s1] | 3-(2-Chlorophenyl)-1-methyl-2-(5-methylthiophen-2-yl)-2,3-dihydroquinazolin-4(1H)-one |
| RN-3-067 | 55 | 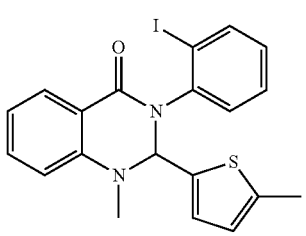 [SMILES: Cc1ccc(C2N(C)c3ccccc3C(=O)N2c2ccccc2I)s1] | 3-(2-Iodophenyl)-1-methyl-2-(5-methylthiophen-2-yl)-2,3-dihydroquinazolin-4(1H)-one |
| RN-3-068 | 56 | 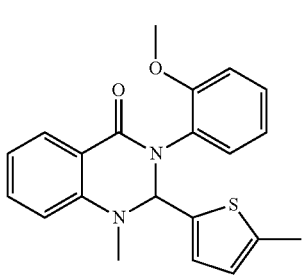 [SMILES: COc1ccccc1N1C(=O)c2ccccc2N(C)C1c1ccc(C)s1] | 3-(2-Methoxyphenyl)-1-methyl-2-(5-methylthiophen-2-yl)-2,3-dihydroquinazolin-4(1H)-one |
| RN-3-069 | 57 | 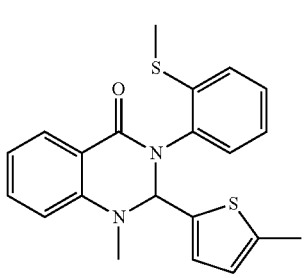 [SMILES: CSc1ccccc1N1C(=O)c2ccccc2N(C)C1c1ccc(C)s1] | 1-Methyl-3-(2-(methylthio)phenyl)-2-(5-methylthiophen-2-yl)-2,3-dihydroquinazolin-4(1H)-one |
| RN-3-070 | 58 | 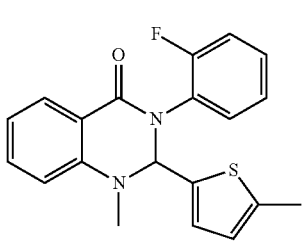 | 3-(2-Fluorophenyl)-1-methyl-2-(5-methylthiophen-2-yl)-2,3-dihydroquinazolin-4(1H)-one |
| RN-3-089 | 59 | 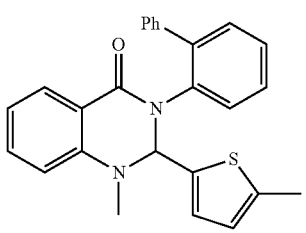 [SMILES: Cc1ccc(C2N(C)c3ccccc3C(=O)N2c2ccccc2-c2ccccc2)s1] | 3-([1,1'-Biphenyl]-2-yl)-1-methyl-2-(5-methylthiophen-2-yl)-2,3-dihydroquinazolin-4(1H)-one |

-continued

| Molecule | Compound | Structure | Name |
|---|---|---|---|
| RN-3-098 | 60 | 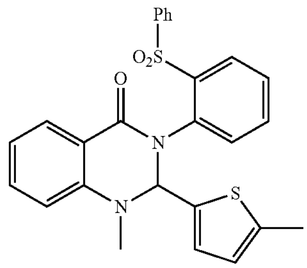 [SMILES: Cc1ccc(C2N(C)c3ccccc3C(=O)N2c2ccccc2S(=O)(=O)c2ccccc2)s1] | 1-Methyl-2-(5-methylthiophen-2-yl)-3-(2-(phenylsulfonyl)phenyl)-2,3-dihydroquinazolin-4(1H)-one |
| RN-3-122 | 61 | 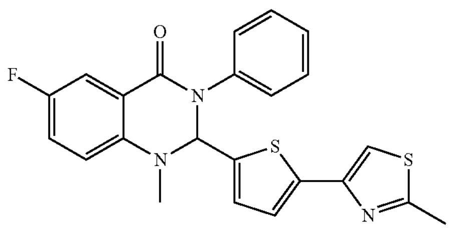 [SMILES: Cc1nc(-c2ccc(C3N(C)c4ccc(F)cc4C(=O)N3c3ccccc3)s2)cs1] | 6-Fluoro-1-methyl-2-(5-(2-methylthiazol-4-yl)thiophen-2-yl)-3-phenyl-2,3-dihydroquinazolin-4(1H)-one |
| RN-3-061 | 62 | 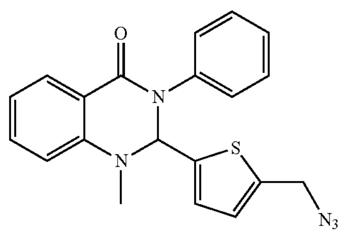 [SMILES: CN1c2ccccc2C(=O)N(c2ccccc2)C1c1ccc(CN=[N+]=[N-])s1] | 2-(5-(Azidomethyl)thiophen-2-yl)-1-methyl-3-phenyl-2,3-dihydroquinazolin-4(1H)-one |
| VP37 | 63 | 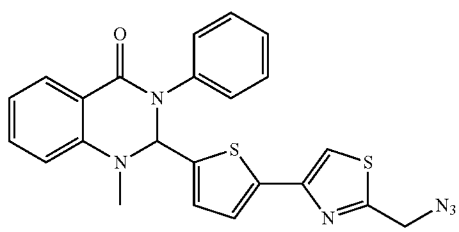 [SMILES: CN1c2ccccc2C(=O)N(c2ccccc2)C1c1ccc(-c2csc(CN=[N+]=[N-])n2)s1] | 2-(5-(2-(Azidomethyl)thiazol-4-yl)thiophen-2-yl)-1-methyl-3-phenyl-2,3-dihydroquinazolin-4(1H)-one |
| VP153 | 64 | 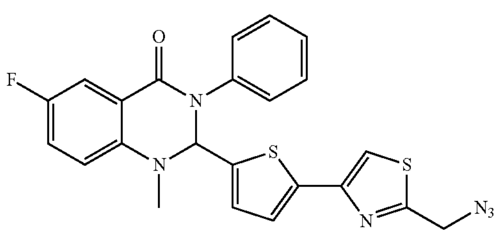 [SMILES: CN1c2ccc(F)cc2C(=O)N(c2ccccc2)C1c1ccc(-c2csc(CN=[N+]=[N-])n2)s1] | 2-(5-(2-(Azidomethyl)thiazol-4-yl)thiophen-2-yl)-6-fluoro-1-methyl-3-phenyl-2,3-dihydroquinazolin-4(1H)-one |
| VP22 | 65 | 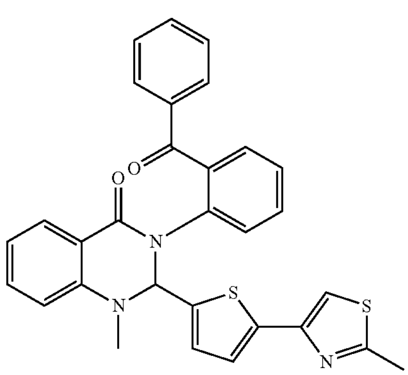 [SMILES: Cc1nc(-c2ccc(C3N(C)c4ccccc4C(=O)N3c3ccccc3C(=O)c3ccccc3)s2)cs1] | 3-(2-Benzoylphenyl)-1-methyl-2-(5-(2-methylthiazol-4-yl)thiophen-2-yl)-2,3-dihydroquinazolin-4(1H)-one |

-continued

| Molecule | Compound | Structure | Name |
|---|---|---|---|
| VP104 | 66 | 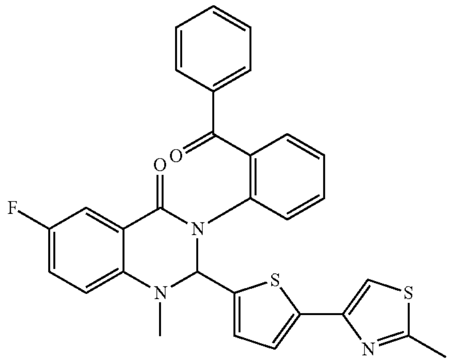 [SMILES: Cc1nc(-c2ccc(C3N(C)c4ccc(F)cc4C(=O)N3c3ccccc3C(=O)c3ccccc3)s2)cs1] | 3-(2-Benzoylphenyl-6-fluoro-1-methyl-2-(5-(2-methylthiazol-4-yl)thiophen-2-yl)-2,3-dihydroquinazolin-4(1H)-one |
| KH071-4 | 67 | 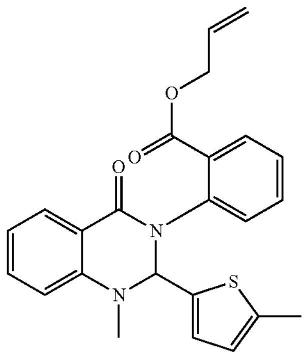 [SMILES: C=CCOC(=O)c1ccccc1N1C(=O)c2ccccc2N(C)C1c1ccc(C)s1] | Allyl 2-(1-methyl-2-(5-methylthiophen-2-yl)-4-oxo-1,4-dihydroquinazolin-3(2H)-yl)benzoate |
| KH093-4 | 68 | 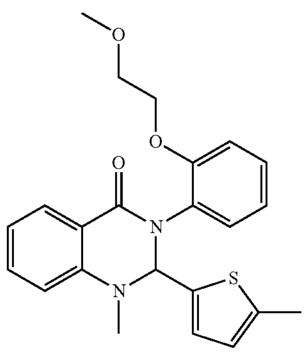 [SMILES: COCCOc1ccccc1N1C(=O)c2ccccc2N(C)C1c1ccc(C)s1] | 3-(2-(2-Methoxyethoxy)phenyl)-1-methyl-2-(5-methylthiophen-2-yl)-2,3-dihydroquinazolin-4(1H)-one |
| KH112-2 | 69 | 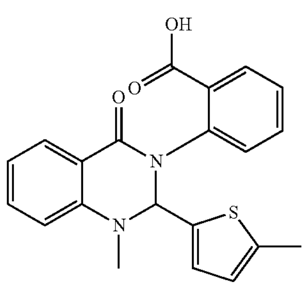 [SMILES: Cc1ccc(C2N(C)c3ccccc3C(=O)N2c2ccccc2C(=O)O)s1] | 2-(1-Methyl-2-(5-methylthiophen-2-yl)-4-oxo-1,4-dihydroquinazolin-3(2H)-yl)benzoic acid |

According to one preferred embodiment of the invention, the compounds of general formula (I) are such that:

$R^1$ is as previously defined: i.e. $R^1$ represents a hydrogen atom, a halogen atom, an alkoxy radical having from 1 to 3 carbon atoms; preferably, $R^1$ is a hydrogen atom or a halogen atom; preferably, $R^1$ is bonded to carbon C7 of the quinazolinone ring;

$R^2$ is a phenyl ring, optionally substituted with: a phenyl radical, a halogen atom, an —$SO_2$-phenyl group, an —S—X or —O—X group, X being an alkyl radical having from 1 to 4 carbon atoms; preferably a methyl radical, an alkoxy having from 1 to 4 carbon atoms, or a PEG of formula —$(CH_2—CH_2—O)_n$—R with n being 1 to 10, preferably n is 1, and R is a hydrogen atom or a methyl radical, preferably R is a methyl radical, or a —CO—Y or —CO—O—Y group, Y being chosen from a hydrogen atom, an alkyl radical having from 1 to 4 carbon atoms, a phenyl ring or an allyl (—$CH_2$—CH═$CH_2$) group;

$R^3$ represents a thiophene ring substituted on C5' of the thiophene, the quinazolinone ring being bonded to C2' of the thiophene, with:
- an alkyl radical having from 1 to 3 carbon atoms, preferably a methyl radical;
- a halogen atom;
- a phenyl radical optionally substituted with an alkoxy radical having from 1 to 3 carbon atoms, a —CN group, an —$NO_2$ group or a —COX or —COOX group with X an alkyl radical having from 1 to 4 carbon atoms, or a combination of these substituents, preferably a methyl radical;
- a —SY group, Y being an alkyl radical having from 1 to 4 carbon atoms or a phenyl radical;
- a —CN group;
- a —$CH_2$—$N_3$ group;
- an aromatic heterocycle having 5 or 6 atoms, which may be chosen from a furan, thiophene, pyrrole, pyrroline, pyrrolidine, dioxolane, oxazole, thiazole, imidazole, imidazoline, imidazolidine, pyrazole, isoxazole, isothiazole, pyran, pyridine, piperidine, dioxane, morpholine, pyridazine, pyrimidine or pyrazine ring, preferably said heterocycle having 5 or 6 atoms is a thiophene, a pyridine, a furan or a thiazole; optionally substituted with at least one alkyl radical having from 1 to 3 carbon atoms and/or a —$CH_2$—$N_3$ group;

$R^4$ is as previously defined, i.e. it represents a hydrogen atom or a methyl radical;

with the exclusion of 3-(4-chlorophenyl)-2-(5-methylthiophen-2-yl)-2,3-dihydroquinazolin-4(1H)-one and of the compound such that $R^1$ is a hydrogen atom, $R^2$ a phenyl radical, $R^3$ a 5-methylthiophen-2-yl radical and $R^4$ a hydrogen atom.

The chemical structure which follows represents the numbering of the carbons used to define the position of the substitutions in the compounds of this preferred embodiment of the invention

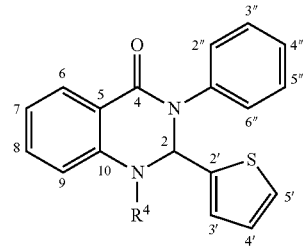

The preferred compounds according to this embodiment of the invention are those chosen from compounds 7, 9, 13, 14, 16 to 28 and 30 to 69.

According to one preferred variant of the preceding embodiment, $R^2$ is a phenyl ring substituted on its carbon C2" (compounds 23, 31, 32, 54 to 60 and 65 to 69) and/or $R^4$ is a methyl radical (compounds 35 to 69).

According to another preferred embodiment of the invention, the compounds of general formula (I) are such that:

$R^1$ is a hydrogen atom or a fluorine atom;

$R^2$ is phenyl ring optionally substituted with: a chlorine, iodine or fluorine atom, an —$OCH_3$, —$SCH_3$ or —$SO_2$-phenyl radical or a phenyl;

$R^3$ is a thiophene radical substituted with a methyl, ethyl, phenyl, —$SCH_3$, 2-thiophene, 2-furan, 3-furan, 2-pyridine or 4-(2-Me thiazole) radical, a bromine atom or S-phenyl, and $R^4$ is a hydrogen atom or a methyl radical;

with the exclusion of the compound such that $R^1$ is a hydrogen atom, $R^2$ a phenyl radical, $R^3$ a 5-methylthiophen-2-yl radical and $R^4$ a hydrogen atom, and their pharmaceutically acceptable salts thereof.

The preferred compounds according to this other embodiment of the invention are those chosen from 7, 9, 13, 17, 18, 19, 20, 21, 25, 31, 32, 34, 35, 36, 37, 38, 39, 40, 41, 42, 43, 44, 47, 54, 55, 56, 57, 58, 59, 60 and 61.

The compounds of general formula (I) for which $R^4$ is a hydrogen atom are obtained from the imine-type compounds which are analogs of Retro-2 (see application EP 2 145 873) by cyclization in a basic medium (route A) or directly by reaction of the anthranilamide with the aldehyde (route B):

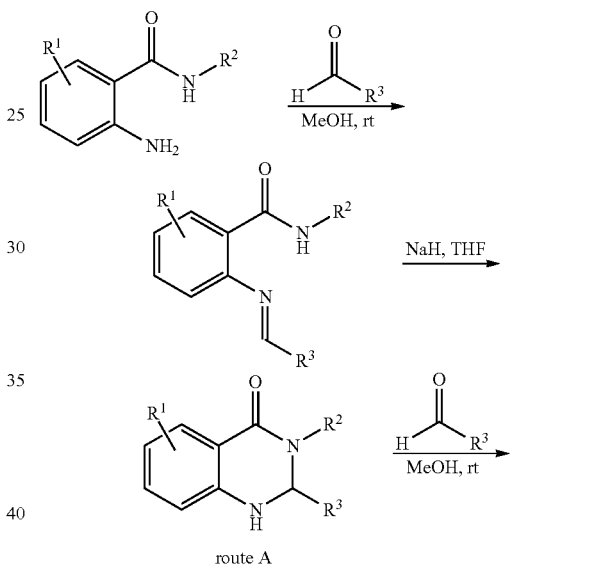

route A

The compounds of general formula such that $R^4$ is a methyl substituent as represented opposite:

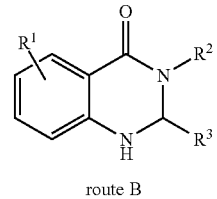

route B

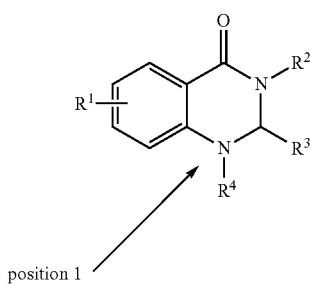

are obtained by deprotonation of the amine in position 1 and trapping of the anion with methyl iodide,

[Chemical scheme: quinazolinone with R¹, R², R³ substituents, NH position, reacted with 1) NaH/THF 2) MeI, THF to give N-Me quinazolinone]

where R¹, R² and R³ are defined as previously.

Some of the compounds according to the invention, in particular compounds 45, 46, 47, 48, 49, 50, 51 and 52, were synthesized via the route described hereinafter:

[Chemical scheme: bromothiophene-substituted quinazolinone reacted with R⁵B(OH)₂, Pd(PPh₃)₄, K₂CO₃, microwave, 1 h, 110° C., DME/H₂O to give product with R³ substituent]

or by coupling of compound 43 with PhSH in the presence of Pd₂dba₃ (0.1 equiv.), dppf (0.15 equiv.) and tBuOK (2 equiv.) in dioxane, for 1 h at 140° C. in a microwave (compound 44) or ZnCN₂ in the presence of Pd₂dba₃ (0.05 equiv.) and dppf (0.1 equiv.) in DMF, for 1 h at 150° C. in a microwave (compound 53).

The compounds according to the invention are pharmacologically active substances and are of interest by virtue of their inhibitory effect on toxins with an intracellular mode of action, in particular ricin.

The use of the compounds of general formula (I), including the various embodiments and the preferred variants thereof, is particularly advantageous for preventing and/or treating disorders caused by toxins with an intracellular mode of action using retrograde transport to poison mammalian eukaryotic cells.

More specifically, the toxins with an intracellular mode of action are: in particular ricin (produced in the seeds of the *Ricinus communis* plant), Shiga toxin and Shiga-like toxins (Stxs) produced by *Shigella dysenteriae* (Stx) and *E. coli* (Stx1 and Stx2), cholera toxin (Ctx from *Vibrio cholerae* responsible for cholera), pertussis toxin (*Bordetella pertussis*, which is the agent responsible for whooping cough), subtilase cytotoxin and thermolabile enterotoxin (*E. coli*).

The use of the compounds according to the invention proves to be effective whether the subject ingests or inhales the toxin or whether the subject is injected with the toxin.

Thus, the compounds according to the invention may be used for preventing and/or treating the poisoning of mammalian eukaryotic cells by toxins with an intracellular mode of action.

Concretely, a toxin such as ricin, when it is inhaled, produces signs of ocular irritation (burning sensation, watering of the eyes, more or less severe conjunctivitis) and pharyngeal irritation and also more or less marked respiratory irritation: cough, dyspnea, pulmonary edema which can result in acute respiratory distress syndrome (ARDS). It should be noted that there is a risk of anaphylactic reaction. The lethal dose is 1 mg/kg of bodyweight (Ministry of Health, France).

Thus, the invention relates to the use of a compound of general formula (I) for preventing and/or treating poisonings with ricin or with other toxins with an intracellular mode of action and protecting eukaryotic cells, in particular epithelial, ocular, pharyngeal, tracheal, bronchial, skin and muscle cells, in particular pulmonary and digestive, preferably intestinal, epithelial cells, of mammals, preferably of humans, against these poisonings.

The invention also relates to pharmaceutical compositions or medicaments comprising one or more compounds of general formula (I) in a pharmaceutically acceptable carrier.

The term "pharmaceutically acceptable" is intended to mean compatible with administration to a subject, preferably a mammal, by any route of administration.

Those skilled in the art will be able to adjust the formulation of the compounds of general formula (I) according to the physicochemical properties thereof and the route of administration thereof.

The medicament may be administered via the oral (in particular in the buccal cavity or by sublingual administration), parenteral, pulmonary, ocular, nasal, etc., route. Other methods of administration that can be envisioned comprise the intraperitoneal (i.p), intravenous (i.v.), subcutaneous (s.c.), intramuscular (i.m.), transcutaneous, transdermal, intracathecal, epidural, submucosal, or nasal or pulmonary inhalation route.

The methods of administration of the compounds of general formula (I) that are preferred are those which use the airway route (nasal or pulmonary inhalation), the oral route (ingestion), the parenteral route or the local (topical) route.

The present invention thus relates to compositions, in particular pharmaceutical compositions, comprising at least one compound of general formula (I) according to the invention and, optionally, a pharmaceutically acceptable carrier, stabilizing excipients and adjuvants conventionally used.

The amount of compound of general formula (I) to be administered to the mammal depends on this compound's own activity, it being possible for said activity to be measured by means which are set out in the examples. This amount also depends on the seriousness of the pathological condition to be treated, in particular on the amount of toxin absorbed and on the route by which it was absorbed; finally, it depends on the age and weight of the individual to be treated.

In addition to the arrangements which precede, the invention also comprises other arrangements that will emerge from the description which follows, which refers to exemplary embodiments of the present invention, and also to the appended figures in which.

EXAMPLES

Figure 1A:
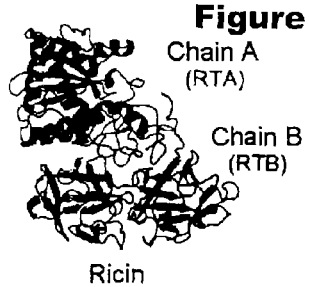
FIG. 1 represents the crystallographic structures of ricin (A, the name of which in the crystallographic structure database is pdb 2AAI) and of Stx2 (B, pdb 1R4P).
Figure 1B:
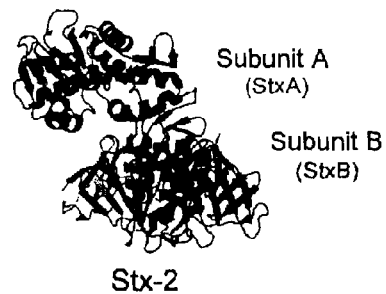
Figure 2A:
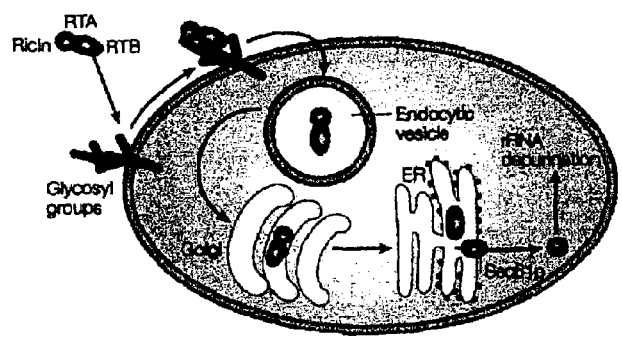
FIG. 2 illustrates diagrammatically the entry and the intracellular trafficking of ricin (A) and of Shiga toxins (B).
Figure 2B:
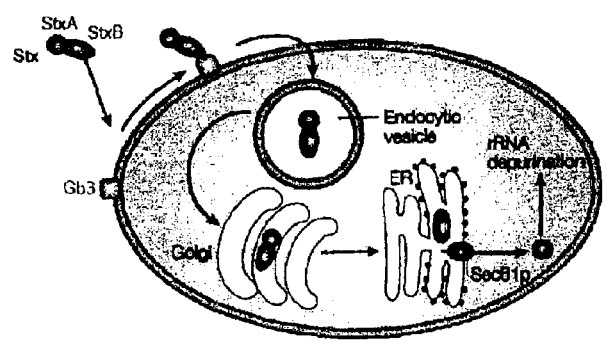

I. Synthesis of Compounds According to the Invention

The compounds of general formula (I) which follow are prepared according to the reaction scheme which follows:

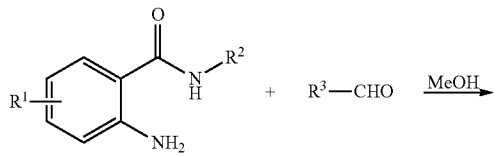

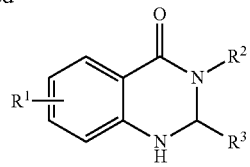

Protocol: 2-aminobenzamide (4.71 mmol), THF (23 ml, 0.2M) and then the aldehyde (4.71 mmol) and para-toluenesulfonic acid (10 mol %, 0.5 mmol) are added to a tube which is sealed. The solution is heated at 75° C. and stirred at this temperature until the starting products have completely disappeared (monitored by thin layer chromatography, typically a reaction time of overnight). After cooling to room temperature, silica is added and the THF is evaporated off Purification by silica gel chromatography followed by evaporation provides the expected products in the form of solids.

TABLE II

Cyclic molecules of 2,3-dihydroquinazolin-4(1H)-one type

| Molecule | Compound | Name | Yield | LC/MS | $^1H$ | $^{13}C$ |
|---|---|---|---|---|---|---|
| RN-1-013 | 1 | 2-(3-Methoxyphenyl)-3-phenyl-2,3-dihydroquinazolin-4(1H)-one | 88% | x | x | x |
| RN-1-019 | 2 | 2-(4-(Dimethylamino)phenyl)-3-phenyl-2,3-dihydroquinazolin-4(1H)-one | 77% | x | x | x |
| RN-1-021 | 3 | 2,3-Diphenyl-2,3-dihydroquinazolin-4(1H)-one | 84% | x | x | x |
| RN-1-027 | 4 | 2-(4-Methoxyphenyl)-3-phenyl-2,3-dihydroquinazolin-4(1H)-one | 78% | x | x | x |
| RN-1-066 | 5 | 2-(3-Methylthiophen-2-yl)-3-phenyl-2,3-dihydroquinazolin-4(1H)-one | 85% | x | x | x |
| RN-1-067 | 6 | 2-(4-Methylthiophen-2-yl)-3-phenyl-2,3-dihydroquinazolin-4(1H)-one | 65% | x | x | x |
| RN-1-068 | 7 | 2-(5-Ethylthiophen-2-yl)-3-phenyl-2,3-dihydroquinazolin-4(1H)-one | 77% | x | x | x |
| RN-1-086 | 8 | 3-((5R,7S)-3-Hydroxyadamantan-1-yl)-2-(5-methylthiophen-2-yl)-2,3-dihydroquinazolin-4(1H)-one | 81% | x | x | x |
| RN-1-100 | 9 | 2-(5-Bromothiophen-2-yl)-3-phenyl-2,3-dihydroquinazolin-4(1H)-one | 91% | x | x | x |
| RN-1-118 | 10 | 2-(5-Methylthiophen-2-yl)-3-(pyridin-3-yl)-2,3-dihydroquinazolin-4(1H)-one | 34% | x | x | x |
| RN-1-120 | 11 | 2-(5-Methylthiophen-2-yl)-3-(pyridin-4-yl)-2,3-dihydroquinazolin-4(1H)-one | 64% | x | x | x |
| RN-1-132 | 12 | 2-(5-Methylthiophen-2-yl)-3-(pyrimidin-4-yl)-2,3-dihydroquinazolin-4(1H)-one | 53% | x | x | x |
| RN-1-148 | 13 | 3-Phenyl-2-(5-phenylthiophen-2-yl)-2,3-dihydroquinazolin-4(1H)-one | 86% | x | x | x |
| RN-1-149 | 14 | 3-([1,1'-Biphenyl]-4-yl)-2-(5-methylthiophen-2-yl)-2,3-dihydroquinazolin-4(1H)-one | 73% | x | x | x |
| RN-1-151 | 15 | 2-(5-Methylthiophen-2-yl)-3-(3-(trifluoromethyl)phenyl)-2,3-dihydroquinazolin-4(1H)-one | 68% | x | x | x |
| RN-1-162 | 16 | 8-Methyl-2-(5-methylthiophen-2-yl)-3-phenyl-2,3-dihydroquinazolin-4(1H)-one | 99% | x | x | x |

TABLE II-continued

Cyclic molecules of 2,3-dihydroquinazolin-4(1H)-one type

| Molecule | Compound | Name | Yield | LC/MS | $^1$H | $^{13}$C |
|---|---|---|---|---|---|---|
| RN-1-173 | 17 | 2-(5-(Methylthio)thiophen-2-yl)-3-phenyl-2,3-dihydroquinazolin-4(1H)-one | 82% | x | x | — |
| RN-1-174 | 18 | 2-([2,2'-Bithiophen]-5-yl)-3-phenyl-2,3-dihydroquinazolin-4(1H)-one | 86% | x | x | x |
| RN-1-175 | 19 | 3-Phenyl-2-(5-(pyridin-2-yl)thiophen-2-yl)-2,3-dihydroquinazolin-4(1H)-one | 72% | x | x | x |
| RN-1-176 | 20 | 2-(5-(Furan-2-yl)thiophen-2-yl)-3-phenyl-2,3-dihydroquinazolin-4(1H)-one | 64% | x | x | x |
| RN-1-177 | 21 | 2-(5-(2-Methylthiazol-4-yl)thiophen-2-yl)-3-phenyl-2,3-dihydroquinazolin-4(1H)-one | 68% | x | x | x |
| RN-2-120 | 22 | 3-(4-Fluorophenyl)-2-(5-methylthiophen-2-yl)-2,3-dihydroquinazolin-4(1H)-one | 80% | x | x | x |
| RN-2-137 | 23 | 3-(2-Fluorophenyl)-2-(5-methylthiophen-2-yl)-2,3-dihydroquinazolin-4(1H)-one | 93% | x | x | x |
| RN-2-161 | 24 | 6-Methoxy-2-(5-methylthiophen-2-yl)-3-phenyl-2,3-dihydroquinazolin-4(1H)-one | 89% | x | x | x |
| RN-2-162 | 25 | 6-Fluoro-2-(5-methylthiophen-2-yl)-3-phenyl-2,3-dihydroquinazolin-4(1H)-one | 70% | x | x | x |
| RN-2-163 | 26 | 7-Fluoro-2-(5-methylthiophen-2-yl)-3-phenyl-2,3-dihydroquinazolin-4(1H)-one | 80% | x | x | x |
| RN-2-177 | 27 | 3-(4-Bromophenyl)-2-(5-methylthiophen-2-yl)-2,3-dihydroquinazolin-4(1H)-one | 80% | x | x | x |
| RN-2-178 | 28 | 3-(3-Bromophenyl)-2-(5-methylthiophen-2-yl)-2,3-dihydroquinazolin-4(1H)-one | 91% | x | x | x |
| RN-2-180 | 29 | 3-(4-Chlorophenyl)-2-(5-methylthiophen-2-yl)-2,3-dihydroquinazolin-4(1H)-one | 89% | x | x | x |
| RN-2-181 | 30 | 3-(3-Chlorophenyl)-2-(5-methylthiophen-2-yl)-2,3-dihydroquinazolin-4(1H)-one | 91% | x | x | x |
| RN-2-183 | 31 | 3-(2-(Methylthio)phenyl)-2-(5-methylthiophen-2-yl)-2,3-dihydroquinazolin-4(1H)-one | 79% | x | x | x |
| RN-2-182 | 32 | 3-(2-Chlorophenyl)-2-(5-methylthiophen-2-yl)-2,3-dihydroquinazolin-4(1H)-one | 92% | x | x | x |
| RN-2-199 | 33 | 6-Iodo-2-(5-methylthiophen-2-yl)-3-phenyl-2,3-dihydroquinazolin-4(1H)-one | 92% | | x | |
| RN-3-121 | 34 | 6-fluoro-2-(5-(2-methylthiazol-4-yl)thiophen-2-yl)-3-phenyl-2,3-dihydroquinazolin-4(1H)-one | 36% | x | x | x |

Synthesis of the compounds of general formula (I) for which $R^4$ is a methyl radical:

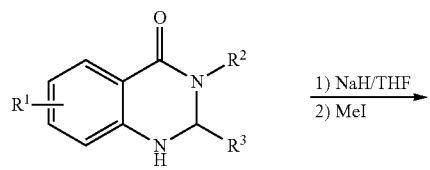

1) NaH/THF
2) MeI

-continued

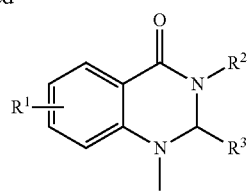

Protocol: a solution of N—H tetrahydroquinazolin-4-ones (1 equiv.) in anhydrous THF (0.5M) is added, dropwise, at 0° C., to a suspension of NaH (1.5 equiv.) in anhydrous tetrahydrofuran (0.3M). After 30 min, iodomethane (1.1 equiv.) is added dropwise. After 10 minutes of reaction, the solution is heated to room temperature and the reaction mixture is stirred for 3 h. The reaction is stopped by adding a saturated solution of NaHCO$_3$. The aqueous phase is extracted with CH$_2$Cl$_2$ (3×50 ml). The organic phases are combined and then washed with a 1M solution of HCl (2×10 ml), dried over anhydrous Na$_2$SO$_4$, filtered and concentrated on a rotary evaporator. Purification by silica gel chromatography provides the expected compounds in the form of solids.

TABLE III

| Molecule | Compound | Name | Yield | LC/MS | $^1$H | $^{13}$C |
|---|---|---|---|---|---|---|
| RN-1-181 | 35 | 1-Methyl-2-(5-methylthiophen-2-yl)-3-phenyl-2,3-dihydroquinazolin-4(1H)-one | 85% starting from RN-1-001 | x | x | x |
| RN-1-186 | 36 | 1-Methyl-3-phenyl-2-(5-phenylthiophen-2-yl)-2,3-dihydroquinazolin-4(1H)-one | 69% starting from RN-1-069 | x | x | x |
| RN-1-192 | 37 | 1-Methyl-3-phenyl-2-(5-(pyridin-2-yl)thiophen-2-yl)-2,3-dihydroquinazolin-4(1H)-one | 97% starting from RN-1-101 | x | x | x |
| RN-1-196 | 38 | 1-Methyl-2-(5-(methylthio)thiophen-2-yl)-3-phenyl-2,3-dihydroquinazolin-4(1H)-one | 91% starting from RN-1-077 | x | x | x |
| RN-1-197 | 39 | 2-([2,2'-Bithiophen]-5-yl)-1-methyl-3-phenyl-2,3-dihydroquinazolin-4(1H)-one | 95% starting from RN-1-080 | x | x | x |
| RN-2-001 | 40 | 2-(5-(Furan-2-yl)thiophen-2-yl)-1-methyl-3-phenyl-2,3-dihydroquinazolin-4(1H)-one | 97% starting from RN-1-104 | x | x | x |
| RN-2-005 | 41 | 2-(5-Ethylthiophen-2-yl)-1-methyl-3-phenyl-2,3-dihydroquinazolin-4(1H)-one | 84% starting from RN-1-068 | x | x | x |
| RN-2-015 | 42 | 1-Methyl-2-(5-(2-methylthiazol-4-yl)thiophen-2-yl)-3-phenyl-2,3-dihydroquinazolin-4(1H)-one | 83% starting from RN-1-105 | x | x | x |
| RN-2-016 | 43 | 2-(5-Bromothiophen-2-yl)-1-methyl-3-phenyl-2,3-dihydroquinazolin-4(1H)-one | 85% starting from RN-1-100 | x | x | x |
| RN-2-019 | 44 | 1-Methyl-3-phenyl-2-(5-(phenylthio)thiophen-2-yl)-2,3-dihydroquinazolin-4(1H)-one | 91% starting from RN-2-016 | x | x | x |
| RN-2-029 | 45 | 2-(5-(3,4-Dimethoxyphenyl)thiophen-2-yl)-1-methyl-3-phenyl-2,3-dihydroquinazolin-4(1H)-one | 88% starting from RN-2-016 | x | x | x |
| RN-2-032 | 46 | 1-Methyl-2-(5-(3-nitrophenyl)thiophen-2-yl)-3-phenyl-2,3-dihydroquinazolin-4(1H)-one | 90% starting from RN-2-016 | x | x | x |
| RN-2-034 | 47 | 2-(5-(Furan-3-yl)thiophen-2-yl)-1-methyl-3-phenyl-2,3-dihydroquinazolin-4(1H)-one | 80% starting from RN-2-016 | x | x | x |
| RN-2-049 | 48 | Methyl 4-(5-(1-methyl-4-oxo-3-phenyl-1,2,3,4-tetrahydroquinazolin-2-yl)thiophen-2-yl)benzoate | 80% starting from RN-2-016 | x | x | x |
| RN-2-050 | 49 | 2-(5-(4-Acetylphenyl)thiophen-2-yl)-1-methyl-3-phenyl-2,3-dihydroquinazolin-4(1H)-one | 89% starting from RN-2-016 | x | x | x |
| RN-2-053 | 50 | 1-Methyl-3-phenyl-2-(5-(3,4,5-trimethoxyphenyl)thiophen-2-yl)-2,3-dihydroquinazolin-4(1H)-one | 73% starting from RN-2-016 | x | x | x |
| RN-2-057 | 51 | 1-methyl-2-(5-(4-methyl-3-nitrophenyl)thiophen-2-yl)-3-phenyl-2,3-dihydroquinazolin-4(1H)-one | 76% starting from RN-2-016 | x | x | x |
| RN-2-059 | 52 | 4-(5-(1-Methyl-4-oxo-3-phenyl-1,2,3,4-tetrahydroquinazolin-2-yl)thiophen-2-yl)benzonitrile | 78% starting from RN-2-016 | x | x | x |
| RN-3-012 | 53 | 5-(1-Methyl-4-oxo-3-phenyl-1,2,3,4-tetrahydroquinazolin-2-yl)thiophene-2-carbonitrile | 68% starting from RN-2-016 | x | | |
| RN-3-066 | 54 | 3-(2-chlorophenyl)-1-methyl-2-(5-methylthiophen-2-yl)-2,3-dihydroquinazolin-4(1H)-one | 67% | | x | x |
| RN-3-067 | 55 | 3-(2-iodophenyl)-1-methyl-2-(5-methylthiophen-2-yl)-2,3-dihydroquinazolin-4(1H)-one | 46% | | x | x |
| RN-3-068 | 56 | 3-(2-methoxyphenyl)-1-methyl-2-(5-methylthiophen-2-yl)-2,3-dihydroquinazolin-4(1H)-one | 28% | | x | x |

TABLE III-continued

| Molecule | Compound | Name | Yield | LC/MS | $^1$H | $^{13}$C |
|---|---|---|---|---|---|---|
| RN-3-069 | 57 | 1-methyl-3-(2-(methylthio)phenyl)-2-(5-methylthiophen-2-yl)-2,3-dihydroquinazolin-4(1H)-one | 73% | x | x | x |
| RN-3-070 | 58 | 3-(2-fluorophenyl)-1-methyl-2-(5-methylthiophen-2-yl)-2,3-dihydroquinazolin-4(1H)-one | 51% | x | x | x |
| RN-3-089 | 59 | 3-([1,1'-biphenyl]-2-yl)-1-methyl-2-(5-methylthiophen-2-yl)-2,3-dihydroquinazolin-4(1H)-one | 74% | x | x | x |
| RN-3-098 | 60 | 1-methyl-2-(5-methylthiophen-2-yl)-3-(2-(phenylsulfonyl)phenyl)-2,3-dihydroquinazolin-4(1H)-one | 65% | x | x | x |
| RN-3-122 | 61 | 6-fluoro-1-methyl-2-(5-(2-methylthiazol-4-yl)thiophen-2-yl)-3-phenyl-2,3-dihydroquinazolin-4(1H)-one | 71% | x | x | x |

II. Measurement of the Protective Activity of the Compounds Against the Toxins on Cells

II. A. Experimental Protocol

Figure 3:
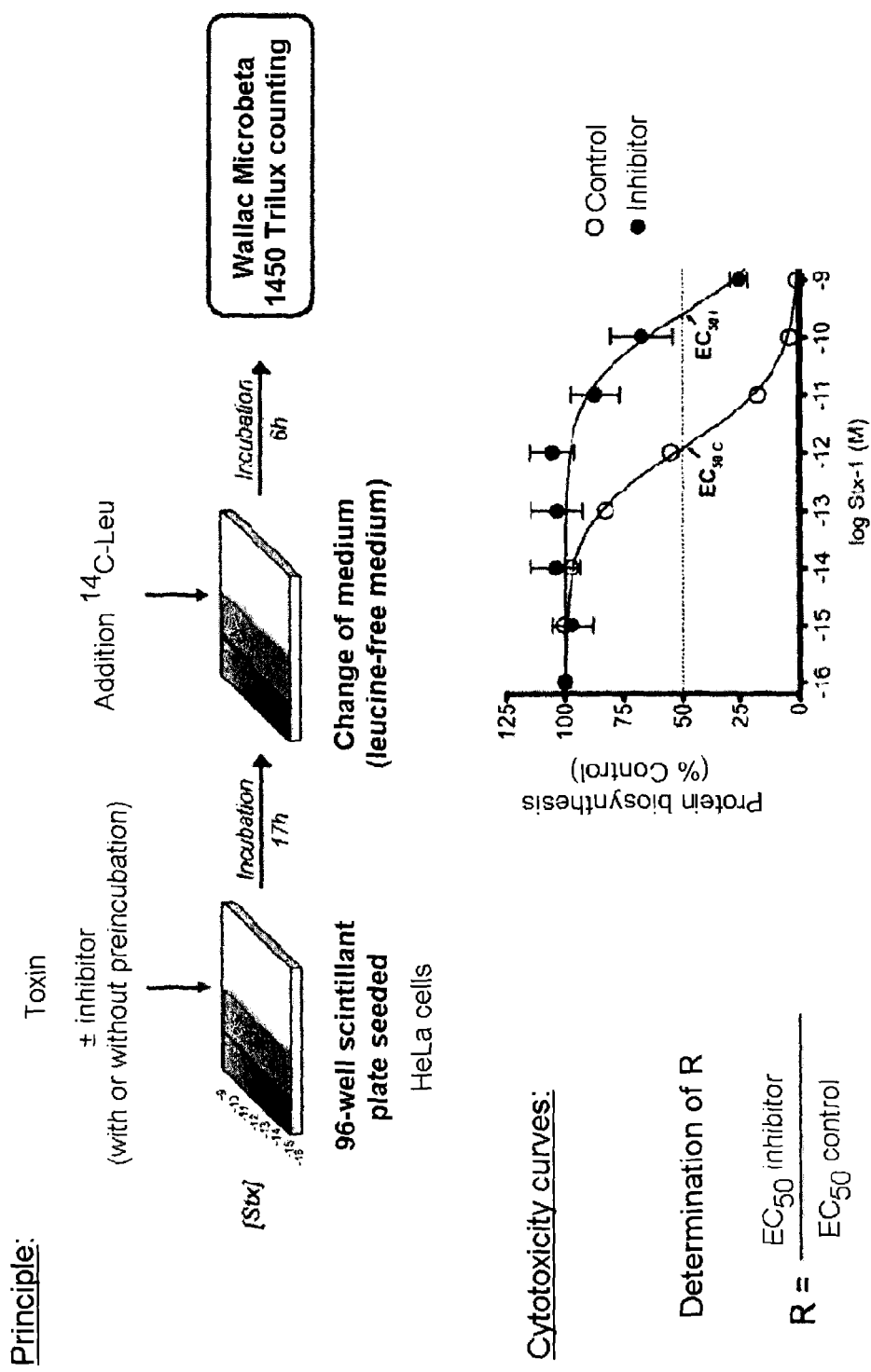
FIG. 3 is a diagrammatic representation of the cell test carried out in the experimental section.

The compounds were tested either on A549 cells (human pulmonary epithelial cells) or on HeLa cells (human uterin cancer cells), respectively against ricin and against Shiga toxins (Stx1 and/or Stx2). The human cells are cultured at 37° C. in an atmosphere containing 5% $CO_2$ in 150 $cm^2$ culture flasks in DMEM medium (Dulbecco's Modified Eagle Medium) containing 100 U/ml of penicillin and 100 µg/ml of streptomycin. The cells are seeded at a density of 50 000 cells per well in Cytostar-T 96-well plates that have a base into which solid scintillant has been incorporated (FIG. 3). The cells (100 µl in complete DMEM: DMEM+ 10% of fetal calf serum (FCS) are preincubated or not preincubated with the inhibitors (50 µl; various concentrations, preincubation of 3 h). The complete medium supplemented with toxin (50 variable concentration range) is then added to each well. After incubation for 20 h, the medium (200 µl) is removed and replaced with a leucine-free DMEM medium (Eurobio) containing 10% of FCS and 0.5 µCi/ml of $^{14}$C-leucine (GE). After incubation for 7 h at 37° C., the incorporation of radioactivity by the cells is determined by reading the plates using a Wallac 1450 Microbeta Trilux scintillation counter (PE).

Since these toxins block protein synthesis, the affected cells are no longer capable of incorporating the radiolabeled leucine. On the other hand, the cells treated with inhibitors still synthesize proteins and therefore incorporate the radiolabeled amino acid. Since the cells concentrate the radioelement sufficiently close to the base of the well, this leads to an excitation of the scintillant contained in the plates and results in the emission of photons, detected by the scintillation counter (measurement in counts per minute, cpm). These data are then expressed as percentage of protein synthesis by the cells. The cytotoxicity curves can thus be plotted (R, FIG. 3), without inhibitor (white surface) or in the presence of inhibitor (black surface). The analysis of the data by nonlinear regression makes it possible to estimate the $EC_{50}$, that is to say the effective concentration for which 50% assimilation of radioactive leucine is observed, which corresponds to 50% of viable cells. The higher the $EC_{50}$ value, the greater the cell protection since a high concentration of toxin is then necessary in order to generate the same cytotoxicity. It is thus possible to determine the effectiveness of the inhibitors by calculating the ratio of the $EC_{50}$ values (R, cf. FIG. 3). The higher the value (>1), the greater the protection of the cells.

Results

Table IV below presents the results in the form of a protective index ($EC_{50}$ compound/$EC_{50}$ ricin ratio): the higher it is, the more the cells are protected against the action of the ricin (protective effect if >1).

TABLE IV

Evaluation of the biological activities of the compounds according to the invention.

| Molecule | Compound | R (ricin) | R (Stx) |
|---|---|---|---|
| Control | Retro-2 | 2.7 | 25 |
| RN-1-068 | 7 | 2.6 | 120 |
| RN-1-100 | 9 | 1.8 | 27.9 |
| RN-1-148 | 13 | 4.2 | 153 |
| RN-1-173 | 17 | 2.8 | 43 |
| RN-1-174 | 18 | 5.6 | 50 |
| RN-1-175 | 19 | 3.1 | 46 |
| RN-1-176 | 20 | 0.7 | 41 |
| RN-1-177 | 21 | 7.3 | 109 |
| RN-2-162 | 25 | — | 133 |
| RN-2-183 | 31 | — | 99 |
| RN-2-182 | 32 | — | 68 |
| RN-3-121 | 34 | — | 295 |
| RN-1-181 | 35 | 6.4 | 80 |
| RN-1-186 | 36 | 6.1 | 29 |
| RN-1-192 | 37 | 4.3 | 111 |
| RN-1-196 | 38 | 4.6 | 60 |
| RN-1-197 | 39 | 4.0 | 36 |
| RN-2-001 | 40 | — | 27 |
| RN-2-005 | 41 | 6.7 | 173 |
| RN-2-015 | 42 | 8.1 | 85 |
| RN-2-016 | 43 | 4.6 | 40 |
| RN-2-019 | 44 | 3.6 | 71 |
| RN-2-034 | 47 | 4.1 | 49 |
| RN-3-066 | 54 | — | 27 |
| RN-3-067 | 55 | — | 25 |
| RN-3-068 | 56 | — | 26 |
| RN-3-069 | 57 | — | 25 |
| RN-3-070 | 58 | — | 25 |
| RN-3-089 | 59 | — | 27 |
| RN-3-098 | 60 | — | 320 |
| RN-3-122 | 61 | — | 40 |

These assays demonstrate that the tested compounds according to the invention provide better protection against ricin and/or Stx than cyclized Retro-2.

Figure 4:
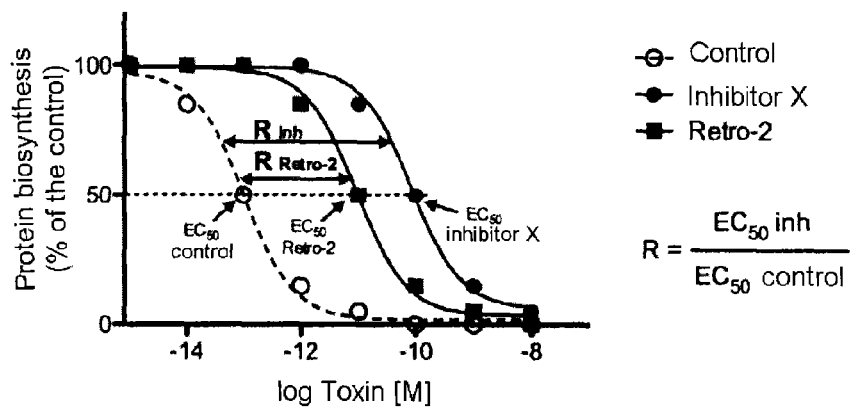
FIG. 4 illustrates the method for determination of R and of the $EC_{50}$ values carried out in part II of the examples.

II.B. Alternative Method for Evaluating the Activity of the Compounds According to the Invention Against Shiga Toxin Table IV above presents the measurement of the inhibitory power of the compounds in the form of a protective index R ($EC_{50}$ toxin+compound/$EC_{50}$ toxin ratio; cf. FIG. 4). The higher the value of R, the more the cells are protected against the action of the toxin. More precise additional data (additional table V hereinafter) are provided for the compounds which have indices R close to that of Retro-2 (R close to 25 in the case of Shiga toxin), in order to dispense in particular with the variability of R.

Indeed, the value of R for a given molecule varies according to experiments. It is not an absolute value and R cannot be used to compare the various molecules with one another, unless they were all tested on the same day in the same experiment. This value only makes it possible to compare the activity of a compound with respect to the control (i.e. Retro-2) and to determine whether or not the molecule is more active in Retro-2 at a given concentration. Indeed, the results in table IV are obtained from experiments carried out with a one and only concentration of compound (30 μM).

The results in the additional table V are based on the study of a range of concentration of each of the compounds tested and are more precise since they make it possible to dispense with the value R and to provide an $IC_{50}$ value which is comparable between all the compounds. $IC_{50}$ corresponds to the concentration of compound which gives 50% of its inhibitory power. The lower this concentration, the more powerful the inhibitor is.

Protocol and Calculation of $IC_{50}$

The test on a 96-well plate is the same as that described in part II.A. above. A whole 96-well plate is required in order to calculate the $IC_{50}$ of each compound.

Six cytotoxicity curves are obtained in the absence and then in the presence of increasing concentrations of the inhibitor. For each concentration (C) of inhibitor, a protection percentage is determined from the value of R calculated by the Prism software with Rmax corresponding to the maximum value of R of the series:

% protection=[(R−1)/(Rmax−1)]×100

Figure 5:
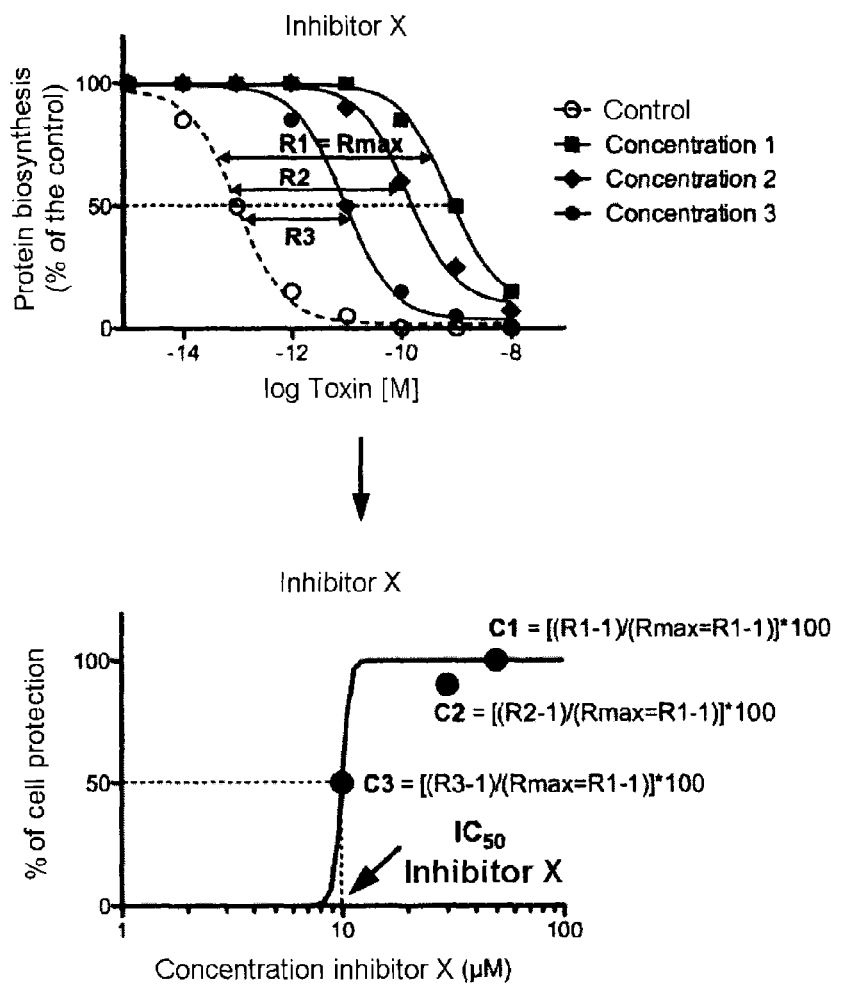
FIG. 5 illustrates the method for calculating the $IC_{50}$ carried out in part II of the examples; the toxicity curves are produced in the absence of inhibitor (Control) and then in the presence of inhibitor at various concentrations.

The $IC_{50}$ is then calculated, using the Prism software by nonlinear regression, from a graph on which is reported, for each concentration of compound, the corresponding cell protection percentage (cf. FIG. 5).

Results

TABLE V

| Molecule | Compound | $IC_{50}$(μM) |
|---|---|---|
| Control | Retro-2 | 27.3 |
| RN-1-100 | 9 | 13.7 |
| RN-2-001 | 40 | 1.5 |
| RN-3-066 | 54 | 8.2 |
| RN-3-067 | 55 | 5.4 |
| RN-3-068 | 56 | 5.4 |
| RN-3-069 | 57 | 3.8 |
| RN-3-070 | 58 | 5.5 |
| RN-3-089 | 59 | 3.7 |
| RN-3-061 | 62 | 12 |
| VP37 | 63 | 3-5 |
| VP153 | 64 | <3 |
| VP22 | 65 | 1-3 |
| VP104 | 66 | 1 |
| KH071-4 | 67 | 13 |
| KH093-4 | 68 | 4.2 |
| KH112-2 | 69 | 11.2 |

Conclusion

These results show that the compounds tested are all more powerful inhibitors of the cellular effect of Shiga toxin than the Retro-2 compound.

III. Demonstration of the Blocking of the Retrograde Transport

Experimental Protocol

The retrograde transport of Shiga toxin subunit B (StxB) for the Golgi apparatus was quantified using a sulfation test described in detail in the literature (Amessou M. et al. *Curr. Protoc. Cell. Biol.* 2006, Chapter 15: Unit 15.10). The principle is the following: a variant of StxB, called StxB-$Sulf_2$, which carries a tandem of protein sulfation recognition sites, is internalized in the presence of $^{35}SO_4^{2-}$. Once StxB-$Sulf_2$ reaches the Golgi apparatus, the sulfotransferases located in the Golgi apparatus catalyze the transfer of the radioactive sulfate onto StxB-$Sulf_2$. After cell lysis, immunoprecipitation and gel electrophoresis, the [$^{35}$S]-StxB-$Sulf_2$ can be detected and quantified by autoradiography. In a previous publication (Stechmann B. et al. *Cell* 2010, 141, 231-24), it was shown that the retrograde transport of cells treated with Retro-1 or Retro-2 was decreased by 90% under certain experimental conditions.

Results

Table VI indicates, for the nontreated cells and the cells treated with various molecules, the measurement of the retrograde transport as a percentage. 100% indicates no effect on retrograde transport, 0% indicates complete blocking of this transport.

TABLE VI

Evaluation of the retrograde transport of cells in the presence of compounds according to the invention.

| Molecule | Compound | % control |
|---|---|---|
| DMSO | | 100 |
| Retro 2 | | 36.9 |
| RN-1-068 | 7 | 13.5 |
| RN-1-148 | 13 | 13.1 |
| RN-1-173 | 17 | 22.8 |
| RN-1-174 | 18 | 17.1 |
| RN-1-175 | 19 | 10.7 |
| RN-1-176 | 20 | 6.5 |
| RN-1-177 | 21 | 0.0 |
| RN-1-186 | 36 | 7.1 |
| RN-1-192 | 37 | 10.3 |
| RN-1-196 | 38 | 18.2 |
| RN-1-197 | 39 | 6.2 |
| RN-2-001 | 40 | 5.3 |
| RN-2-005 | 41 | 0.0 |
| RN-2-015 | 42 | 0.0 |

CONCLUSION

The compounds above show a marked retrograde transport blocking activity, greater than that of Retro-2, which can be explained either by good affinity for the target and/or good internalization into the cell, or by good stability of these compounds in a biological medium.

The invention claimed is:

1. A compound of formula (I):

(I)

[Chemical structure: quinazolinone with substituents $R^1$, $R^2$, $R^3$, $R^4$]

wherein:

R¹ represents a hydrogen atom, a halogen atom or an alkoxy radical having from 1 to 3 carbon atoms;

R² represents a phenyl ring, optionally substituted with: a phenyl radical, a halogen atom, an —SO₂-phenyl group or an —S—X or —O—X group, X being an alkyl radical having from 1 to 4 carbon atoms, an alkoxy having from 1 to 4 carbon atoms or a PEG of formula —(CH₂—CH₂—O)ₙ—R with n being 1 to 10, and R is a hydrogen atom or a methyl radical, or a —CO—Y or —CO—O—Y group, Y being a hydrogen atom, an alkyl radical having from 1 to 4 carbon atoms, a phenyl ring or an allyl (—CH₂—CH=CH₂) group;

R³ represents a thiophene ring substituted on C5' of the thiophene, the quinazolinone ring being bonded to C2' of the thiophene, with
- an alkyl radical having from 1 to 3 carbon atoms;
- a halogen atom;
- a phenyl radical optionally substituted with an alkoxy radical having from 1 to 3 carbon atoms, a —CN group, an —NO₂ group or a —COX or —COOX group with X an alkyl radical having from 1 to 4 carbon atoms, or a combination of these substituents;
- an —SY group, Y being an alkyl radical having from 1 to 4 carbon atoms or a phenyl radical;
- a —CN group;
- a —CH₂—N₃ group;
- an aromatic heterocycle having 5 or 6 atoms selected from the group consisting of a furan, a thiophene, a pyrrole, a pyrroline, a pyrrolidine, a dioxolane, oxazole, a thiazole, an imidazole, an imidazoline, an imidazolidine, a pyrazole, an isoxazole, an isothiazole, a pyran, a pyridine, a piperidine, a dioxane, a morpholine, a pyridazine, a pyrimidine and a pyrazine ring, optionally substituted with at least one alkyl radical having from 1 to 3 carbon atoms, a —CH₂—N₃, group, or both;

R⁴ represents a hydrogen atom or a methyl radical; and with the exclusion of 3-(4-chlorophenyl)-2-(5-methylthiophen-2-yl)-2,3-dihydroquinazolin-4(1H)-one and of the compound such that R¹ is a hydrogen atom, R² a phenyl radical, R³ a 5-methylthiophen-2-yl radical and R⁴ a hydrogen atom.

2. The compound of claim 1, which is selected from the group consisting of

| Molecule | Compound | Name |
| --- | --- | --- |
| RN-1-068 | 7 | 2-(5-Ethylthiophen-2-yl)-3-phenyl-2,3-dihydroquinazolin-4(1H)-one |
| RN-1-100 | 9 | 2-(5-Bromothiophen-2-yl)-3-phenyl-2,3-dihydroquinazolin-4(1H)-one |
| RN-1-148 | 13 | 3-Phenyl-2-(5-phenylthiophen-2-yl)-2,3-dihydroquinazolin-4(1H)-one |
| RN-1-149 | 14 | 3-([1,1'-Biphenyl]-4-yl)-2-(5-methylthiophen-2-yl)-2,3-dihydroquinazolin-4(1H)-one |
| RN-1-162 | 16 | 8-Methyl-2-(5-methylthiophen-2-yl)-3-phenyl-2,3-dihydroquinazolin-4(1H)-one |
| RN-1-173 | 17 | 2-(5-(Methylthio)thiophen-2-yl)-3-phenyl-2,3-dihydroquinazolin-4(1H)-one |
| RN-1-174 | 18 | 2-([2,2'-Bithiophen]-5-yl)-3-phenyl-2,3-dihydroquinazolin-4(1H)-one |
| RN-1-175 | 19 | 3-Phenyl-2-(5-(pyridin-2-yl)thiophen-2-yl)-2,3-dihydroquinazolin-4(1H)-one |
| RN-1-176 | 20 | 2-(5-(Furan-2-yl)thiophen-2-yl)-3-phenyl-2,3-dihydroquinazolin-4(1H)-one |
| RN-1-177 | 21 | 2-(5-(2-Methylthiazol-4-yl)thiophen-2-yl)-3-phenyl-2,3-dihydroquinazolin-4(1H)-one |
| RN-2-120 | 22 | 3-(4-Fluorophenyl)-2-(5-methylthiophen-2-yl)-2,3-dihydroquinazolin-4(1H)-one |
| RN-2-137 | 23 | 3-(2-Fluorophenyl)-2-(5-methylthiophen-2-yl)-2,3-dihydroquinazolin-4(1H)-one |
| RN-2-161 | 24 | 6-Methoxy-2-(5-methylthiophen-2-yl)-3-phenyl-2,3-dihydroquinazolin-4(1H)-one |
| RN-2-162 | 25 | 6-Fluoro-2-(5-methylthiophen-2-yl)-3-phenyl-2,3-dihydroquinazolin-4(1H)-one |
| RN-2-163 | 26 | 7-Fluoro-2-(5-methylthiophen-2-yl)-3-phenyl-2,3-dihydroquinazolin-4(1H)-one |
| RN-2-177 | 27 | 3-(4-Bromophenyl)-2-(5-methylthiophen-2-yl)-2,3-dihydroquinazolin-4(1H)-one |
| RN-2-178 | 28 | 3-(3-Bromophenyl)-2-(5-methylthiophen-2-yl)-2,3-dihydroquinazolin-4(1H)-one |
| RN-2-181 | 30 | 3-(3-Chlorophenyl)-2-(5-methylthiophen-2-yl)-2,3-dihydroquinazolin-4(1H)-one |
| RN-2-183 | 31 | 3-(2-(Methylthio)phenyl)-2-(5-methylthiophen-2-yl)-2,3-dihydroquinazolin-4(1H)-one |
| RN-2-182 | 32 | 3-(2-Chlorophenyl)-2-(5-methylthiophen-2-yl)-2,3-dihydroquinazolin-4(1H)-one |
| RN-2-199 | 33 | 6-Iodo-2-(5-methylthiophen-2-yl)-3-phenyl-2,3-dihydroquinazolin-4(1H)-one |
| RN-3-121 | 34 | 6-Fluoro-2-(5-(2-methylthiazol-4-yl)thiophen-2-yl)-3-phenyl-2,3-dihydroquinazolin-4(1H)-one |
| RN-1-181 | 35 | 1-Methyl-2-(5-methylthiophen-2-yl)-3-phenyl-2,3-dihydroquinazolin-4(1H)-one |
| RN-1-186 | 36 | 1-Methyl-3-phenyl-2-(5-phenylthiophen-2-yl)-2,3-dihydroquinazolin-4(1H)-one |
| RN-1-192 | 37 | 1-Methyl-3-phenyl-2-(5-(pyridin-2-yl)thiophen-2-yl)-2,3-dihydroquinazolin-4(1H)-one |

-continued

| Molecule | Compound | Name |
|---|---|---|
| RN-1-196 | 38 | 1-Methyl-2-(5-(methylthio)thiophen-2-yl)-3-phenyl-2,3-dihydroquinazolin-4(1H)-one |
| RN-1-197 | 39 | 2-([2,2'-Bithiophen]-5-yl)-1-methyl-3-phenyl-2,3-dihydroquinazolin-4(1H)-one |
| RN-2-001 | 40 | 2-(5-(Furan-2-yl)thiophen-2-yl)-1-methyl-3-phenyl-2,3-dihydroquinazolin-4(1H)-one |
| RN-2-005 | 41 | 2-(5-Ethylthiophen-2-yl)-1-methyl-3-phenyl-2,3-dihydroquinazolin-4(1H)-one |
| RN-2-015 | 42 | 1-Methyl-2-(5-(2-methylthiazol-4-yl)thiophen-2-yl)-3-phenyl-2,3-dihydroquinazolin-4(1H)-one |
| RN-2-016 | 43 | 2-(5-Bromothiophen-2-yl)-1-methyl-3-phenyl-2,3-dihydroquinazolin-4(1H)-one |
| RN-2-019 | 44 | 1-Methyl-3-phenyl-2-(5-(phenylthio)thiophen-2-yl)-2,3-dihydroquinazolin-4(1H)-one |
| RN-2-029 | 45 | 2-(5-(3,4-Dimethoxyphenyl)thiophen-2-yl)-1-methyl-3-phenyl-2,3-dihydroquinazolin-4(1H)-one |
| RN-2-032 | 46 | 1-Methyl-2-(5-(3-nitrophenyl)thiophen-2-yl)-3-phenyl-2,3-dihydroquinazolin-4(1H)-one |
| RN-2-034 | 47 | 2-(5-(Furan-3-yl)thiophen-2-yl)-1-methyl-3-phenyl-2,3-dihydroquinazolin-4(1H)-one |
| RN-2-049 | 48 | Methyl 4-(5-(1-methyl-4-oxo-3-phenyl-1,2,3,4-tetrahydroquinazolin-2-yl)thiophen-2-yl)benzoate |
| RN-2-050 | 49 | 2-(5-(4-Acetylphenyl)thiophen-2-yl)-1-methyl-3-phenyl-2,3-dihydroquinazolin-4(1H)-one |
| RN-2-053 | 50 | 1-Methyl-3-phenyl-2-(5-(3,4,5-trimethoxyphenyl)thiophen-2-yl)-2,3-dihydroquinazolin-4(1H)-one |
| RN-2-057 | 51 | 1-methyl-2-(5-(4-methyl-3-nitrophenyl)thiophen-2-yl)-3-phenyl-2,3-dihydroquinazolin-4(1H)-one |
| RN-2-059 | 52 | 4-(5-(1-Methyl-4-oxo-3-phenyl-1,2,3,4-tetrahydroquinazolin-2-yl)thiophen-2-yl)benzonitrile |
| RN-3-012 | 53 | 5-(1-Methyl-4-oxo-3-phenyl-1,2,3,4-tetrahydroquinazolin-2-yl)thiophene-2-carbonitrile |
| RN-3-066 | 54 | 3-(2-Chlorophenyl)-1-methyl-2-(5-methylthiophen-2-yl)-2,3-dihydroquinazolin-4(1H)-one |
| RN-3-067 | 55 | 3-(2-Iodophenyl)-1-methyl-2-(5-methylthiophen-2-yl)-2,3-dihydroquinazolin-4(1H)-one |
| RN-3-068 | 56 | 3-(2-Methoxyphenyl)-1-methyl-2-(5-methylthiophen-2-yl)-2,3-dihydroquinazolin-4(1H)-one |
| RN-3-069 | 57 | 1-Methyl-3-(2-(methylthio)phenyl)-2-(5-methylthiophen-2-yl)-2,3-dihydroquinazolin-4(1H)-one |
| RN-3-070 | 58 | 3-(2-Fluorophenyl)-1-methyl-2-(5-methylthiophen-2-yl)-2,3-dihydroquinazolin-4(1H)-one |
| RN-3-089 | 59 | 3-([1,1'-Biphenyl]-2-yl)-1-methyl-2-(5-methylthiophen-2-yl)-2,3-dihydroquinazolin-4(1H)-one |
| RN-3-098 | 60 | 1-Methyl-2-(5-methylthiophen-2-yl)-3-(2-(phenylsulfonyl)phenyl)-2,3-dihydroquinazolin-4(1H)-one |
| RN-3-122 | 61 | 6-Fluoro-1-methyl-2-(5-(2-methylthiazol-4-yl)thiophen-2-yl)-3-phenyl-2,3-dihydroquinazolin-4(1H)-one |
| RN-3-061 | 62 | 2-(5-(Azidomethyl)thiophen-2-yl)-1-methyl-3-phenyl-2,3-dihydroquinazolin-4(1H)-one |
| VP37 | 63 | 2-(5-(2-(Azidomethyl)thiazol-4-yl)thiophen-2-yl)-1-methyl-3-phenyl-2,3-dihydroquinazolin-4(1H)-one |
| VP153 | 64 | 2-(5-(2-(Azidomethyl)thiazol-4-yl)thiophen-2-yl)-6-fluoro-1-methyl-3-phenyl-2,3-dihydroquinazolin-4(1H)-one |
| VP22 | 65 | 3-(2-Benzoylphenyl)-1-methyl-2-(5-(2-methylthiazol-4-yl)thiophen-2-yl)-2,3-dihydroquinazolin-4(1H)-one |
| VP104 | 66 | 3-(2-Benzoylphenyl)-6-fluoro-1-methyl-2-(5-(2-methylthiazol-4-yl)thiophen-2-yl)-2,3-dihydroquinazolin-4(1H)-one |
| KH071-4 | 67 | Allyl 2-(1-methyl-2-(5-methylthiophen-2-yl)-4-oxo-1,4-dihydroquinazolin-3(2H)-yl)benzoate |
| KH093-4 | 68 | 3-(2-(2-Methoxyethoxy)phenyl)-1-methyl-2-(5-methylthiophen-2-yl)-2,3-dihydroquinazolin-4(1H)-one, and |
| KH112-2 | 69 | 2-(1-Methyl-2-(5-methylthiophen-2-yl)-4-oxo-1,4-dihydroquinazolin-3(2H)-yl)benzoic acid. |

3. The compound of claim 1, wherein $R^2$ is a phenyl ring substituted on its carbon C2".

4. The compound of claim 2, which is selected from the group consisting of
3-(2-Fluorophenyl)-2-(5-methylthiophen-2-yl)-2,3-dihydroquinazolin-4(1H)-one,
3-(2-(Methylthio)phenyl)-2-(5-methylthiophen-2-yl)-2,3-dihydroquinazolin-4(1H)-one,
3-(2-Chlorophenyl)-2-(5-methylthiophen-2-yl)-2,3-dihydroquinazolin-4(1H)-one,
3-(2-Chlorophenyl)-1-methyl-2-(5-methylthiophen-2-yl)-2,3-dihydroquinazolin-4(1H)-one,
3-(2-Iodophenyl)-1-methyl-2-(5-methylthiophen-2-yl)-2,3-dihydroquinazolin-4(1H)-one,
3-(2-Methoxyphenyl)-1-methyl-2-(5-methylthiophen-2-yl)-2,3-dihydroquinazolin-4(1H)-one,
1-Methyl-3-(2-(methylthio)phenyl)-2-(5-methylthiophen-2-yl)-2,3-dihydroquinazolin-4(1H)-one,
3-(2-Fluorophenyl)-1-methyl-2-(5-methylthiophen-2-yl)-2,3-dihydroquinazolin-4(1H)-one, 3-([1,1'-Biphenyl]-2-yl)-methyl-2-(5-methylthiophen-2-yl)-2,3-dihydroquinazolin-4(1H)-one,
1-Methyl-2-(5-methylthiophen-2-yl)-3-(2-(phenylsulfonyl)phenyl)-2,3-dihydroquinazolin-4(1H)-one,
3-(2-Benzoylphenyl)-1-methyl-2-(5-(2-methylthiazol-4-yl)thiophen-2-yl)-2,3-dihydroquinazolin-4(1H)-one,
3-(2-Benzoylphenyl)-6-fluoro-1-methyl-2-(5-(2-methylthiazol-4-yl)thiophen-2-yl)-2,3-dihydroquinazolin-4(1H)-one,
Allyl 2-(1-methyl-2-(5-methylthiophen-2-yl)-4-oxo-1,4-dihydroquinazolin-3(2H)-yl)benzoate,
3-(2-(2-Methoxyethoxy)phenyl)-1-methyl-2-(5-methylthiophen-2-yl)-2,3-dihydroquinazolin-4(1H)-one, and
2-(1-Methyl-2-(5-methylthiophen-2-yl)-4-oxo-1,4-dihydroquinazolin-3(2H)-yl)benzoic acid.

5. The compound of claim 1, wherein $R^4$ is a methyl radical.

6. The compound of claim 2, which is selected from group consisting of
1-Methyl-2-(5-methylthiophen-2-yl)-3-phenyl-2,3-dihydroquinazolin-4(1H)-one,
1-Methyl-3-phenyl-2-(5-phenylthiophen-2-yl)-2,3-dihydroquinazolin-4(1H)-one,
1-Methyl-3-phenyl-2-(5-(pyridin-2-yl)thiophen-2-yl)-2,3-dihydroquinazolin-4(1H)-one,
1-Methyl-2-(5-(methylthio)thiophen-2-yl)-3-phenyl-2,3-dihydroquinazolin-4(1H)-one,
2-([2,2'-Bithiophen]-5-yl)-1-methyl-3-phenyl-2,3-dihydroquinazolin-4(1H)-one,
2-(5-(Furan-2-yl)thiophen-2-yl)-1-methyl-3-phenyl-2,3-dihydroquinazolin-4(1H)-one,
2-(5-Ethylthiophen-2-yl)-1-methyl-3-phenyl-2,3-dihydroquinazolin-4(1H)-one,
1-Methyl-2-(5-(2-methylthiophen-2-yl)-3-phenyl-2,3-dihydroquinazolin-4(1H)-one,
2-(5-Bromothiophen-2-yl)-1-methyl-3-phenyl-2,3-dihydroquinazolin-4(1H)-one,
1-Methyl-3-phenyl-2-(5-(phenylthio)thiophen-2-yl)-2,3-dihydroquinazolin-4(1H)-one,
2-(5-(3,4-Dimethoxyphenyl)thiophen-2-yl)-1-methyl-3-phenyl-2,3-dihydroquinazolin-4(1H)-one,
1-Methyl-2-(5-(3-nitrophenyl)thiophen-2-yl)-3-phenyl-2,3-dihydroquinazolin-4(1H)-one,
2-(5-(Furan-3-yl)thiophen-2-yl)-1-methyl-3-phenyl-2,3-dihydroquinazolin-4(1H)-one,
Methyl 4-(5-(1-methyl-4-oxo-3-phenyl-1,2,3,4-tetrahydroquinazolin-2-yl)thiophen-2-yl)benzoate,
2-(5-(4-Acetylphenyl)thiophen-2-yl)-1-methyl-3-phenyl-2,3-dihydroquinazolin-4(1H)-one,
1-Methyl-3-phenyl-2-(5-(3,4,5-trimethoxyphenyl)thiophen-2-yl)-2,3-dihydroquinazolin-4(1H)-one,
1-methyl-2-(5-(4-methyl-3-nitrophenyl)thiophenyl-2-yl)-3-phenyl-2,3-hydroquinazolin-4(1H)-one,
4-(5-(1-Methyl-4-oxo-3-phenyl-1,2,3,4-tetrahydroquinazolin-2-yl)thiophen-2-yl)benzonitrile,
5-(1-Methyl-4-oxo-3-phenyl-1,2,3,4-tetrahydroquinazolin-2-yl)thiophene-2-carbonitrile,
3-(2-Chlorophenyl)-1-methyl-2-(5-methylthiophen-2-yl)-2,3-dihydroquinazolin-4(1H)-one,
3-(2-Iodophenyl)-1-methyl-2-(5-methylthiophen-2-yl)-2,3-dihydroquinazolin-4(1H)-one,
3-(2-Methoxyphenyl)-1-methyl-2-(5-methylthiophen-2-yl)-2,3-dihydroquinazolin-4(1H)-one,
1-Methyl-3-(2-(methylthio)phenyl)-2-(5-methylthiophen-2-yl)-2,3-dihydroquinazolin-4(1H)-one,
3-(2-Fluorophenyl)-1-methyl-2-(5-methylthiophen-2-yl)-2,3-dihydroquinazolin-4(1H)-one,
3-([1,1'-Biphenyl]-2-yl)-1-methyl-2-(5-methylthiophen-2-yl)-2,3-dihydroquinazolin-4(1H)-one,
1-Methyl-2-(5-methylthiophen-2-yl)-3-(2-(phenylsulfonyl)phenyl)-2,3-dihydroquinazolin-4(1H)-one,
6-Fluoro-1-methyl-2-(5-(2-methylthiazol-4-yl)thiophen-2-yl)-3-phenyl-2,3-dihydroquinazolin-4(1H)-one,
2-(5-(Azidomethyl)thiophen-2-yl)-1-methyl-3-phenyl-2,3-dihydroquinazolin-4(1H)-one,
2-(5-(2-(Azidomethyl)thiazol-4-yl)thiophen-2-yl)-1-methyl-3-phenyl-2,3-dihydroquinazolin-4(1H)-one,
2-(5-(2-(Azidomethyl)thiazol-4-yl)thiophen-2-yl)-6-fluoro-1-methyl-3-phenyl-2,3-dihydroquinazolin-4(1H)-one,
3-(2-Benzoylphenyl)-1-methyl-2-(5-(2-methylthiazol-4-yl)thiophen-2-yl)-2,3-dihydroquinazolin-4(1H)-one,
3-(2-Benzoylphenyl)-6-fluoro-1-methyl-2-(5-(2-methylthiazol-4-yl)thiophen-2-yl)-2,3-dihydroquinazolin-4(1H)-one,
Allyl 2-(1-methyl-2-(5-methylthiophen-2-yl)-4-oxo-1,4-dihydroquinazolin-3(2H)-yl)benzoate,
3-(2-(2-Methoxyethoxy)phenyl)-1-methyl-2-(5-methylthiophen-2-yl)-2,3-dihydroquinazolin-4(1H)-one, and
2-(1-Methyl-2-(5-methylthiophen-2-yl)-4-oxo-1,4-dihydroquinazolin-3(2H)-yl)benzoic acid.

7. A method for preventing and/or treating disorders induced by toxins with an intracellular mode of a using retrograde transport, the method comprising administering to a subject in need thereof an effective amount of at least one compound of formula (I):

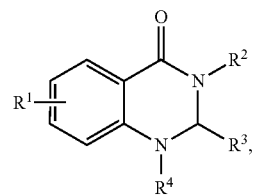

to a subject in need thereof,
wherein:
$R^1$ represents a hydrogen atom, a halogen atom or an alkoxy radical having from 1 to 3 carbon atoms;
$R^2$ is a phenyl ring, optionally substituted with: a phenyl radical, a halogen atom, an —$SO_2$-phenyl group or an —S—X or —O—X group, X being an alkyl radical having from 1 to 4 carbon atoms, alkoxy having from 1 to 4 carbon atoms; or a PEG of formula —$(CH_2—CH_2—O)_n$—R with n being 1 to 10, and R represents a hydrogen atom or a methyl radical, or a —CO—Y or —CO—O—Y group, Y being a hydrogen atom, an alkyl radical having from 1 to 4 carbon atoms, a phenyl ring or an allyl (—$CH_2$—CH=$CH_2$) group;
$R^3$ represents a thiophene ring substituted on C5' of the thiophene, the quinazolinone ring being bonded to C2' of the thiophene, with
an alkyl radical having from 1 to 3 carbon atoms;
a halogen atom;
a phenyl radical optionally substituted with an alkoxy radical having from 1 to 3 carbon atoms, a —CN group, an —$NO_2$ group or a —COX or —COOX group with X an alkyl radical having from 1 to 4 carbon atoms, or a combination of these substituents;

an —SY group, Y being an alkyl radical having from 1 to 4 carbon atoms or a phenyl radical;

a —CN group;

a —CH$_2$—N$_3$ group;

an aromatic heterocycle having 5 or 6 atoms selected from the group consisting of a furan, a thiophene, a pyrrole, a pyrroline, a pyrrolidine, a dioxolane, oxazole, a thiazole, an imidazole, an imidazoline, an imidazolidine, a pyrazole, an isoxazole, an isothiazole, a pyran, a pyridine, a piperidine, a dioxane, a morpholine, a pyridazine, a pyrimidine and a pyrazine ring, optionally substituted with at least one alkyl radical having from 1 to 3 carbon atoms, a —CH$_2$—N$_3$ group, or both; and R$^4$ represents a hydrogen atom or a methyl radical;

with the exclusion of the compound such that R$^1$ is a hydrogen atom, R$^2$ a phenyl radical, R$^3$ a 5-methylthiophen-2-yl radical and R$^4$ a hydrogen atom.

8. The method of claim 7, wherein R$^2$ is a phenyl ring substituted on its carbon C2".

9. The method of claim 7, wherein R$^4$ is a methyl radical.

10. The method of claim 7, wherein the toxins with an intracellular mode of action are selected from the group consisting of ricin, Shiga toxin and Shiga-like toxins (Stxs) produced by *Shigella dysenteriae* (Stx) and *E. coli* (Stx1 and Stx2), cholera toxin (Ctx from *Vibrio cholerae* responsible for cholera), pertussis toxin (*Bordetella pertussis*, the agent responsible for whooping cough), subtilase cytotoxin and thermolabile enterotoxin (*E. coli*).

11. A pharmaceutical composition or a medicament, comprising at least one compound of formula (I) as defined in claim 1, in a pharmaceutically acceptable carrier, wherein said pharmaceutical composition or said medicament is adapted to be administered by an airway route, an oral route, a parenteral route or a local route.

12. A pharmaceutical composition or a medicament, comprising at least one compound of 1 formula (I) as defined in claim 7, in a pharmaceutically acceptable carrier, wherein said pharmaceutical composition or said medicament is adapted to be administered by an airway route, an oral route, a parenteral route or a local route.

* * * * *